US007214525B1

(12) United States Patent
Jarrett et al.

(10) Patent No.: US 7,214,525 B1
(45) Date of Patent: May 8, 2007

(54) PESTICIDAL AGENTS

(75) Inventors: Paul Jarrett, Warwickshire (GB); Deborah June Ellis, Warwickshire (GB); James Alun Wynne Morgan, Swansea (GB)

(73) Assignee: University of Warwick, Coventry (GB)

(*) Notice: Subject to any disclaimer, the term of this patent is extended or adjusted under 35 U.S.C. 154(b) by 0 days.

(21) Appl. No.: 09/242,843

(22) PCT Filed: Aug. 27, 1997

(86) PCT No.: PCT/GB97/02284

§ 371 (c)(1), (2), (4) Date: Nov. 18, 1999

(87) PCT Pub. No.: WO98/08388

PCT Pub. Date: Mar. 5, 1998

(30) Foreign Application Priority Data

Aug. 29, 1996 (GB) ................................ 9618083.1

(51) Int. Cl.

| | |
|---|---|
| ***C12P 21/06*** | (2006.01) |
| ***C12P 21/04*** | (2006.01) |
| ***C12N 1/20*** | (2006.01) |
| ***C07H 1/00*** | (2006.01) |
| *C07H 21/04* | (2006.01) |

(52) U.S. Cl. ................. 435/252.3; 435/69.1; 435/71.1; 435/252.33; 435/252.5; 536/23.1; 536/23.7; 530/350

(58) Field of Classification Search ................ 530/300, 530/350; 536/23.1, 23.7; 435/320.1, 243, 435/252.31

See application file for complete search history.

(56) References Cited

U.S. PATENT DOCUMENTS 5,616,318 A 4/1997 Dudney
5,770,192 A * 6/1998 Cayley et al.

FOREIGN PATENT DOCUMENTS

| | | |
|---|---|---|
| EP | 0823215 | 2/1998 |
| WO | WO8401775 | 5/1984 |
| WO | WO9500647 | 1/1995 |
| WO | WO9717432 | 5/1997 |
| WO | WO9850427 | 11/1998 |

OTHER PUBLICATIONS

Z. Glinski et al, Efforts to Induce Defence Responses in the Greater Wax Moth larvae by Oral Feeding of Insect Pathogenic Bacteria, 1986, Comp. Biochem. Physiol., vol. 85A, No. 4, pp. 673-677.*

Yamanaka, Satoshi et al., Chemical Abstracts, CA No. 118:3550, Jan. 4, 1993.

Bowen, David Joseph et al., STN-International/UMI Company, STN-AN 96: 33246, DISSABS Order No. AAI9608671 (1995) [Abstract].

H. Matsui et al., Nucleic Acids Research, 18: 2181-2 (1990).

F. Binder et al., Gene, 47: 267-77 (1986).

* cited by examiner

*Primary Examiner*—Sean McGarry
(74) *Attorney, Agent, or Firm*—Dann, Dorfman, Herrell and Skillman, P.C.

(57) ABSTRACT

A method for killing pests (e.g. insects) comprising administering material from *Xenorhabdus* species (e.g. *X. nematophilus*) such as cells or supernatants orally to the pests, either alone or in conjunction with *Bacillus thuringiensis* or pesticidal materials derived therefrom. Also disclosed is an isolated pesticidal agent (and compositions comprising the same) characterized in that it is obtainable from cultures of *X. nematophilus* or mutants thereof, has oral pesticidal activity agent *Pieris brassicae, Pieris rapae* and *Plutella xylostella*, is substantially heat stable to 55° C., is proteinaceous, acts synergistically with *B. thuringiensis* cells as an oral pesticide and is substantially resistant to proteolysis by trypsin and proteinase K. DNA encoding pesticidal activity is also disclosed.

12 Claims, 12 Drawing Sheets

% MORTALITY
100
80
60
40
20
0
OD (600nm)
2.5
2
1.5
1
0.5
0
0
10
20
30
40
50
TIME (HOURS)
CELLS SUPERNATANTS GROWTH

Fig.2.

```
   1 TCCACAATTG CCGGAGAAAA TCAGTCGGGA ACTGCCGGTG ATTATTCGTC ACTTATTAAA
  61 CGAATTTGCC GACCAGAATA AGGCTAAAAA ACTGCTACAG GCGCAACGCG ACTCGAACGA
 121 AGCGTTAACG GTAAAGAGTC ATTCGGATCC GCTGTATCGC TTTTGTGGTT ATCTGGTGTC
 181 TGTCAATGAT ATGACCGGAA TGAAGATGGG CAATAAAAAC ATTAGCCCAC GAGCACCGAG
 241 ATTGTACTTG TATCATGCCT ATCTCTCTTT TATGGAAGCG CACGGCTTTG AACGTCCGTT
 301 AACACTGACT AAGTTTGGTG AATCCATCCC CAAGATTATG CTGGAATACC GGAAGGAGTA
 361 TCGAAAAGTG CGAACCAAGA AAGGCTATTC CTATAACGTG GAATTATCGG AAGAGGCCGA
 421 AGAATGGCTA CCGTCAGTGC CTGAGTGTCG AGACTTTAAA TCACCTGTAT AAAACTTTGA
 481 GCTTTAAGTC TGCACTCCAT ACACAACTTA AAATATCTAA TTGTATTTAA AAGAAAATAA
 541 TAGATGTATA GTTATTTTTT AACTATACAT AAGCTCTACA TGCTCTTCAT TCGTGTAAAA
 601 AATGGGTGAA CAGGTGATAC AGTCAGTGAA TATCATATTA ATTACCGTAA ACCCAGATGT
 661 AGCAAGGCTT TCAGGGAATT GTGCAGAGGG TGCATAACTG AGAGGGTGAA AAAGATTTTC
 721 AGGGGGGCTT ATGGCAGGTA AACAAAATCA GAAGCAAATA CCGTGCACAA TCTGGTTTTT
 781 ATTTTTTGGT ACTACCTCAA ATTAAAATGA TGTAATCATC TGATTTTATT TAAGAATAGA
 841 AGTTAATCAC AATTTCATTG ATGGACTTTC ATTCACACTG GTATAGATAA ATAATTCTGT
 901 TATATCCTGT TTCATTACGC ATTCATCAGG AGTGCTGTTA CAGGAGACAA GAATGTCACA
 961 CATCATTTAC TTGTCGTTAA AGGGCAAGAA GCAGGGTTTA ATTTCAGCGG GTTGTTCAAC
1021 GCCTGAATCA ATTGGAAATC GCTATCAAAA AGGACGTGAA GATCAAATAC AGGTATTGAG
1081 CCTGAATCAT TCGATGAGCC GTGACCAGAA TGTTAATCAT CAACCCGTCA GTTTTGTGAA
1141 ACCCATTGAT AAATCCTCTC CCCTGTTTGC TGGATGCCAG TTTTGTGCAT TACAGGACAA
1201 GCCAGATGGG ACAACTGGAG TTCTTTTATG AAATCAAGCT GACCAGTGCC ACGATTGTGG
1261 ATATTTCCTA TAATTATCCG GCATTCAATC AATGATAATG GTGCGATACC CCATGAAGTG
1321 GTGATGCTCG ATTATAAGTC CATTTCATGC AACCACATCG CCGCAGGACT TCGGGCTACA
1381 GCATACGCAA TTAGCCGGAA GTGAAGAAGC AAGCCGCTTT TATCTGGGGT CTCGAATGTT
1441 AAGCCACTTA AGAAGCCGCT GGTTGAAGAA ACCCCGGTAA AACCCGCTAA ACATCATGCC
1501 CGTTATCGTT GTGTGGATGA TGACGGCAAT CTTTTAACCG AACGCAAGTA TCGGGTTTGC
1561 CTGCCGGATG GTCAGATAAA AGAAGGAAAG ACTGATAAAC AAGGTTACAC CCAATGGCAT
1621 CTTACGGATG ACAAAAATAA ACTTGAATTT CATATTTTAA AGGATTAATA CCATGCCAGC
1681 CTATACCGTT CAGACAAAAA TAGAATCCAA CGTACCTGTT GAAAACCTGC TTTACGACTT
1741 AACCATTTAT CGTAAGGATG CAAAAGGAAA TTTCCATATC TTGCTTGATG TTTTTCAGGA
1801 GAAACTACAG AGTAATTATG AAACACAACA GCATATCACG CAGGAAATAG ACGACGATCT
1861 TTCTGTGATT TATATTATGC AAATTATGCT TCACCGCAAA CATGGCTCAA ATATATTTCC
1921 GGCACTGCAA ACCCATTTTA AGAAAATGTA TACCCTCGGT GAATTAACTT CCGGTAAAGC
1981 CTGTTCGGAG AAAAAACGGG AAAATGCCTG TTATTTTGAA AGTACAGTTG AAACAAAACC
2041 TGTCAGCGAC GGGGATAATA CCGTTGACTT AAATATCACT ATTCCTGAAC GACCTTTTAT
2101 TGCCAAAGAA TATCCCATTG GTCACCCACA CGATCCATTT GAAAAAAGTA AAATTGAATC
2161 ATAAATACAG GACAGGTTAT CGAAAAGAAT TTATCCGGAT CAAAATGGAG CAAGTTTATG
2221 TCAGGGCGCG AGCACACTAT TTTAGCTGCG TTTTTAAGAT GATTATCTCT TAATGTTCAG
2281 TTTTAATAGT GTTTTTATCG AGTGAAATTT AATCGCACAG GCAATTCTTT AGACTTTTAT
2341 AGAAAACTAA AGAATTAAAG AACAAGATTG ACATTTTAAG TTCAAATATT AATCAAAGTA
2401 TGCTCGCGCC CTGAGTTTAT GTGGCCCTGC CGCTTTTTTT TATTGCCTGC CAATAGATAG
2461 ACCAGATATT TATGAGCAAG CGGCACGAGA ATTATGGCAA TATGGCCGAA CTAAAATTGG
2521 TCAACTGGAA ATTAAGCCGG GTGAGGGTTG CCGACATCCT AAAGGTACTT TTTATAATCA
2581 ATATGGTGAA AGAATATCTG GGTTAGATTG GCTGACATTG GCAAGCCTAA GAGATTCAGA
2641 AAATATGATG ATGAGGTTGA TGATGAAGTA GCTGGTATTA CAATGTGGGG AAAATTGACA
2701 GAATGGTTTG AAAAATCAGG GTATGAAAAA GTATTTAGTA ATGTCGGCTT ATCCCATTCT
2761 AATATAAATG ACATAGTAAC TCTTAGTGAT TACTATAACA AAGGATATCA TGTTGTTACT
2821 TTGATTTCAG CAGGAATGTT ATCAGATTTT GGTGACATAG AAACATCAGG AAAAAATCAT
2881 TGGATAGTTT GGGAAGGAGT AGTAGAAAAC TATGAGAAAG AAAATATCAC AAATAATTCA
2941 GATCTGAATC AATATGTAAA TTTAAATCTG TTTTCATGGG GTAAAGTGGA ACATCAAATT
3001 AAAAAAAACA AATCACTAGA TTATGTACTC AACCATATTT TTTGAGGGTT GGTTTTTAAA
3061 CCAATGAAAT AACATGAAAA AAATATTAAT TATTTTTATT TTTTTACTTT ATGGTTGTGG
3121 TAATCCAACG CCAAAAGTTT TACCAAAATC AGAGTTTCTT CCTGATGCAG TGATAAATGA
3181 ACCATATCAG GCATCAATTA CCATCACAGG AGGTGCATTG AATGAAAAAA GCGTTTGGGT
3241 AAAAATTCAT CCTACTGGCT CAGGACTAAC ATGGAATCCA AAAGATAGTT CTTTCCTATA
3301 GGGTGGAAAA AAAGAAATAA GAAAAGATTA TCATCATATA AATATAACAG GTACCCCAAA
3361 GAAGACAGAA TTGATAAAAA TTGAAGTGGT AGGATTTACA TTGGGTACAA TGTACGCACG
3421 GAAAGAGTTC ACTATAAATT ATACTATAAA AGTAAGGGAA TAATTGTCAC TATCAGAATG
3481 GTGATTTAAT TCGCCATTTT TATACTTTTG TATACTCTCT CAACATAATC AGGATTCTTT
```

Fig.2.

```
3541 CTTATTATTT TTCATGGTGC TAAAAACGTT TATTGCAAAA ATAAATTAAG TTAATCAGAT
3601 AAATTATCTG CATTACTGTT ATAATCGATA ACACGATAAC CTGACTTTCT GCCTGTTCTT
3661 ATGAACTCGA AGATAATCCT TTCTGAGCCT GAACGAATCA CATTGCAACC ACTCGCTTTG
3721 AATCACCCAC ACCGGGACAT TCGTACGCGA GGAACGGGTT TACTCATGCT TGCCAGAGGG
3781 AGCAAGCCGT CCCAGATCAC CGCTGAAATC GGATGCAGTC TCCGGGTTAT CTGTAATTGG
3841 GTTCACATGT GGCACAGATA GCGGGATTAT TCGGCGGTCA TGCCGGAGGC CGGTATCTCG
3901 CCATGACGCC TGACATGATT GCCACTGCGC TCGAAGCCGC CAGCGCAGAG TCCCTGACGT
3961 GCGTCGAAGC CAGGCAGGGT TTCCCTGCCT TGTACGCTTG AAACGCTGGC GAATACCCTG
4021 AAAAAACAGG GGCTCCCCTA TAAACGCCCC CGCCTGTCGC TTAAAAAAAG CGCAATAAAA
4081 CGGAGTTTGC TGAAAAATCC GCCTTGCTGA ATAAAATTAA GGCCGGAGCA CAGTCAGGAC
4141 ATTACCGTCT GGTCTATTTT GAGTTCTGGG GGCGTTAAAT TACACGGATA ACACGCTGTT
4201 TTACCAGACA ACGTCAGGCA GTATCACGCG AGATGACGTG ATTGATTTTT TAGAGCCGGT
4261 GGCCAGACAA GGGACAACCG CCTGACATTT TTAGTGTTGG ATAATGCGCG TATCCATCAC
4321 GGGATAGAGG AAAAAATCAG AAATGGCGGG TGACGAGAAC ACAACCTGTT TTTATTCTAT
4381 CTTCCCGCTT ACAGCCCAGA GCTGTATCTG ATTGAAATCG TCTGGAAACA GGCCAAATAC
4441 GACTGGCGAC GTTTTATCAC CTGGACTCAG GATACAATGG AATATGAGGT AAATACTTTA
4501 TTGAAAGGTT ATGGCGACCA ATTTGCAATT AACTTTTCTT GAGTACTTAG TAAGAATAGA
4561 GTCAGTCGAG GTTTTTTCAT TTCGGGTCGT GGGGATGATA CTGAAAATTT GTTTGTAATC
4621 TCTGAAAATT GCTGTTTCTG TGGCTACGTC TGTCTTTTGG GATATTGTTT CCATCAAGTC
4681 TGTCAACATA CTGTTAAGTT AGATGTTGAT AAAAGAGACT GAATTATAAT ACAAAACAAT
4741 AAATCACTTG GACAATATTT TATTTCACAT GAGACATTAA GGTTGATTTT CCCAATCTGG
4801 TCAGTTATAA CCGAATAAGG ATCTTGAAAA ATCATGGGAT CTTACTTTTA TCAAATGAAG
4861 TTAACGTAAA AGTTGATAAA GAAAATTATT TAATTCTAAG TGCCGTTGGC ATAAATATTT
4921 TGTGTTTTGT TAATGAATGA ATAACCAGGT AAGCTGGATT TTCATTTTTT AATTACTCGT
4981 TACAATATGC TATTTATTTA TATAAAGAGT TTGTGCCCAT TTAACCAGTA AACAAATTTG
5041 TTCAACCGTA ACTTAGCTTC ATCGACTTTT GGCCTCGCCT GGTCAGAATC TAGGGCCGTT
5101 ATCCTATTTA TTTATGATAA ATAAAATTTA ATTATCTTTA ATAAGCTGAA TATGTGGATT
5161 TGTGCTCAAT CTTGGATTCA AGTATGTATT CCTTTTGGTA CCCTGCTTTA TTTTAAGGCA
5221 GATGAAGAGG ATGCCAACAT GACACAATAT CGATTACGAC TGTAACATTA AAGTCAGTTA
5281 TAAATTTTAT GATTAAAATG AAATTTTAGT AGAAAATCGT ATTCTATTCC GCCATTTACA
5341 ATAGCATCCT CTTTAATATC ATTAATCTCA GATAAAACAA ATAATTACAA TGTGAATAGA
5401 ATAATGACTT ACAAAATAAG CACTAAATCT TCAGATGAAC TCTTAACTGA CAACACTATT
5461 TTATAAAATA ATTGAGGTTA TTATGTATAG CACGGCTGTA TTACTCAATA AAATCAGTCC
5521 CACTCGCGAC GGTCAGACGA TGACTCTTGC GGATCTGCAA TATTTATCCT TCAGTGAACT
5581 GAGAAAAATC TTTGATGACC AGCTCAGTTG GGGAGAGGCT CGCCATCTCT ATCATGAAAC
5641 TATAGAGCAG AAAAAAAATA ATCGCTTGCT GGAAGCGCGT ATTTTTACCC GTGCCAACCC
5701 ACAATTATCC GGTGCTATCC GACTCGGTAT TGAACGAGAC AGCGTTTCAC GCAGTTATGA
5761 TGAAATGTTT GGTGCCCGTT CTTCTTCCTT TGTGAAACCG GGTTCAGTGG CTTCCATGTT
5821 TTCACCGGCT GGCTATCTCA CCGAATTGTA TCGTGAAGCG AAGGACTTAC ATTTTTCAAG
5881 CTCTGCTTAT CATCTTGATA ATCGCCGTCC GGATCTGGCT GATCTGACTC TGAGCCAGAG
5941 TAATATGGAT ACAGAAATTT CCACCCTGAC ACTGTCTAAC GAACTGTTGC TGGAGCTATT
6001 ACCCGCAAGA CCGGAGGTGA TTCGGACGCA TTGATGGAGA GCCTGTCAAC TTACCGTCAG
6061 GCCATTGATA CCCCTTACCA TCAGCCTTAC GAGACTATCC GTCAGGTCAT TATGACCCAT
6121 GACAGTACAC TGTCAGCGCT GTCCCGTAAT CCTGAGGTGA TGGGGCAGGC GGAAGGGGCT
6181 TCATTACTGG CGATTCTGGC CAATATTTCT CCAGAACTGT ATAACATTTT GACCGAAGAG
6241 ATTACGGAAA AGAACGCTGA TGCTTTATTT GCGCAAAACT TCAGTGAAAA TATCACGCCC
6301 GAAAATTTCG CGTCACAATC ATGGATAGCC AAGTATTATG GTCTTGAACT TTCTGAGGTG
6361 CAAAAATACC TCGGGATGTT GCAGAATGGC TATTCTGACA GCACCTCTGC TTATGTGGAT
6421 AATATCTCAA CGGGTTTAGT GGTCAATAAT GAAAGTAAAC TCGAAGCTTA CAAAATAACA
6481 CGTGTAAAAA CAGATGATTA TGATAAACAT GTAAATTACT TTGATCTGAT GTATGAAGGA
6541 AATAATCAAT TCTTTATATG TGCTAATTTT AAGATATCGA GAGAATTTGG GGCGACTCTT
6601 AGGAAAAACT CAGGGACAAG TGGCATTGTC GGCAGCCTTT CCGGTCCCCT GGTAGCCAAT
6661 ACTAATTTCA AAAGCAATTA CTTAAGTAAC ATATCTGATA ATGAATACAG AAATGGCGTA
6721 AAAATATATG CCTATCGCTA TACGTCTTCC ACCAGCGCCA CAAATCAGGG CGGCGGAATA
6781 TTCACTTTTG AGTCTTATCC CCTGACTATA TTTGCGCTCA AACTGAATAA AGCCATTCGC
6841 TTGTGCCTGA CTAGCGGGCT TTCACCGAAT GAACTGCAAA CTATCGTACG CAGTGACAAT
6901 GCACAAGGCA TCATCAACGA CTCCGTTCTG ACCAAAGTTT TCTATACTCT GTTCTACAGT
6961 CACCGTTATG CACTGAGCTT TGATGATGCA CAGGTACTGA ACGGATCGGT CATTAATCAA
7021 TATGCCCGAC GATGACAGTG TCAGTCATTT TAACCGTCTC TTTAATACCC CGCCGCTGAA
7081 AGGGAAAATC TTTGAAGCCG ACGGCAACAC GGTCAGCATT GATCCGGATG AAGAACAATC
7141 TACCTTTGCC CGTTCAGCCC TGATGCGTGG TCTGGGGATC AACAGTGGTG AACTGTATCA
7201 GTTAGGCAAA CTGGCGGGTG TATTGGACAC ACAAAATATC CTCACACTTT CTGTCCCTGT
7261 TATATCTTCA CTGTATCGCC TCACGTTACT GGCCCGTGCC CATCAGCTGA CGGTTAATGA
7321 ACTGTGTATG CTTTATGGTT TTTCGCCGTT CAATGGCAAA ACAACGGCTT CTTTGTCTTC
```

Fig.2.

```
7381  CGGGGAGTTG TCACGGCTGG TTATCTGGTT GTATCAGGTG ACGCAGTGGC TGACTGAGGG
7441  CGGAAATCAC CACTGAAGCG ATCTGGTTAT TATGTACGCC AGAGTTCAGC GGGAATATTT
7501  CACCGGAAAT CAGTAATCTG CTTAATACTC TCCGACCCCG TATTAGTGAA GACATGGCAC
7561  AAAGTAGTGA CCGGGAGCTT CAGGCTGAAA TTCTCGCGCC GTTTATTGCT GCAACGCTGC
7621  ATCTGGCGTC ACCAGATATG GCGCGGTATA TCCTGTTGTG GACTGATAAC CTGCGGCCGG
7681  GCGGCCTGAA TATCGCCGGA TTTATGATGC TGGTGCTGAA AGAGACGCTG AGTGATGAGG
7741  AAACGACCCA ACTGGTTCAA TTCTGCCATG TAATGGCACA GTTATCGCTT TCCGTGCAGA
7801  CACTGCGTCT CAGTGAAGCA GAGCTTTCTG TGCTGGTCAT TTCCGATTTT GTGGTACTGG
7861  GTGCGAGAAG CCAACCGCCG GACAACACAA TATTGATACT CTGTTCTCAC TCTACCGATT
7921  CCACCAGTGG ATTAATGGGC TGGGAAATCC CGGCTCTGAC ACGCTGGATA TGCTGCGCCA
7981  AGCAGACACT CACGGGCGAC AGACTGGGCC TCCGTGATGG GGCTGGACAT CAGTATGGTA
8041  ACGCAGGCCA TGGGTTCCCG CCGGCGTGAA CCAACTTCAG TGTTGGCAGG ATATCAACCC
8101  CGTGTTGCAG TGGATACATG TGGCATCAGC ACTGCTCACT GATGCCGTCG GTTATCCGTA
8161  CGCTGGTGAA TATCCGTTAC GTGACTGCAT TAAACAAAGC CGAGTCGAAT CTGCCTGCCT
8221  GGGATAAGTG GCAGACGCTG GCAGAAAATA TGGCAGCCGG ACTGAGTACA CAACAGGCTC
8281  AGACGCTGGC GGATTATACC GCAGAGCGCC TGAGTAACGT GTTGTGCAAT TGGTTTCTGG
8341  CGAATATCCA GCCAGAAGGG GTGTCCCTGC ACAGCCGGGA TGACCTGTAC AGCTATTTCC
8401  TGATTGATAA TCAGGTCTCT TCTGCCATAA AAACCACCCG ACTGGCAGAG GCCATTGCCG
8461  GTATTCAGCT CTACATCAAC CGGGCGCTGA ACCGGATAGA GCCTAATGCC CGTGCCGATG
8521  TGTCAACCCG CCAGTTTTTT ACCGACTGGA CGGTGAATAA CCGTTACAGC ACCTGGGGCG
8581  GGGTGTCGCG GCTGGTTTAT TATCCGGAAA ATTACATTGA CCCGACCCAG CGTATCGGGC
8641  AGACCCGGAT GATGGATGAA CTGCTGGAAG ATATCAGCCA GAGTCAGCTC AGCCGGGACA
8701  CGGTGGAAGA GGCCTTTAAA ACTTACCTGA CCGCTTTGAA ACCGTGGCAG ACCTGAAAGT
8761  TGTCAGCGCT ATCACCGACA ACGTCAACAG CAACACCGGA CTGACCTGGT TTGTCGGCCA
8821  AACGCGGGAG AACCTGCCGG AATATTACTG GCGTAACGTG CATATATCAC GGATGCAGGC
8881  GGGTGAACTG GCCGCCGATG CCTGGAAAGA TTGGACGAAG ATTGATACAG CGGTCAACCC
8941  ATACAAGGAT GCAATACGTC CGGTCATATT CAGGGAACGT TTGCACCTTA TCGTGGGTAG
9001  AAAAAGAGGA AGTGGCGAAA AATGGTACTG ATCCGGTGGA AACCTATGAC CGTTTTACTC
9061  TGAAACTGGC GTTTCTGCGT CATGATGGCA GTTGGAGTGC CCCCTGGTCT TACGATATCA
9121  CAACGCAGGT GGAGGCGGTC ACTGACAAAA AACCTGACAC TGAACGGCTG GCGCTGGCCG
9181  CATCAGGCTT TCAGGGCGAG GATACTCTGC TGGTGTTTGT GTACAAAACC GGGGTGAGTT
9241  ACCCGGATTT TGGCGACAAC AATAAAAATG TGGCAGGCAT GACCATTTAC GGCGATGGCT
9301  CCTTCAAAAA GATGGAGAAC ACAGCACTCA GCGTTACAGC CAACTGAAAA ATACCTTTGA
9361  TATCATTCAT ACTCAAGGCA ACGACTTGGT AAGAAAGGCC AGCTATCGTT TCGCGCAGGA
9421  TTTTGAAGTG CCTGCCTCGT TGAATATGGG TTCTGCCATC GGTGATGATA GTCTGACGGT
9481  GATGGAAAAC GGGAATATTC CGCAGATAAC CAGTAAATAC TCCAGCGATA ACCTTGCTAT
9541  TACGCTACAT AACGCCGCTT TCACTGTCAG ATATGATGGC AGTGGCAATG TCATCAGAAA
9601  CAAACAAATC AGCGCCATGA AACTGACGGG GTTGGATGAA AGTCCCAGTA CGGCAATGCA
9661  TTTATCATCG CAAATACCGT TAAACATTAT GGCGGTTACT CTGATCTGGG GGGCCCGATC
9721  ACCGTTTTTA TTAAAACGGA AAAACTATAT TGCATCAGTT CAAGGCCACT TGATGAACGC
9781  AGATTACACT AGGCGTTTGA TTCTAACACC AGTTGAAAAT AATTATTATG CCAGATTGTT
9841  CGAGTTTCCA TTTTCTCCAA ACACAATTTT AAACACCGTT TTCACGGTTG GTAGCAATAA
9901  AACCAGTGAT TTTAAAAAGT GCAGTTATGC TGTTGATGGT AATAATTCTC AGGGCTTCCA
9961  GATATTTAGT TCCTATCAAT CATCCGGCTG GCTGGATATT GACACAGGTA TTAACAATAC
10021 TGATGTCAAA ATTACGGTGG TAGCTGGCAG TAAAACCCAC ACCTTTACGG CCAGTGACCA
10081 TATTGCTTCC TTGCCGGCAA ACAGTTTTGA TGCTATGCCG TACACCTTTA AGCCACTGGA
10141 AATCGATGCT TCATCGTTGG CCTTTACCAA TAATATTGCT CCTCTGGATA TCGTTTTTGA
10201 GACCAAAGCC AAAGACGGGC GAGTGCTGGG TAAGATCAAG CAAACATTAT CGGTGAAACG
10261 GGTAAATTAT AATCCGGAAG ATATTCTGTT TCTGCGTGAA ACTCATTCGG GTGCCCAATA
10321 TATGCAGCTC GGGGTGTATC GTATTCGTCT TAATACCCTG CTGGCTTCTC AACTGGTATC
10381 CAGAGCAAAC ACGGGCATTG ATACTATCCT GACAATGGAA ACCCAGCGGT TACCGGAACC
10441 TCCGTTGGGA GAAGGCTTCT TTGCCAACTT TGTTCTGCCT AAATATGACC CTGCTGAACA
10501 TGGCGATGAG CGGTGGTTTA AAATCCATAT CGGGAATGTT GGCGGTAACA CGGGAAGGCA
10561 GCCTTATTAC AGCGGAATGT TATCCGATAC GTCGGAAACC AGTATGACAC TGTTTGTCCC
10621 TTATGCCGAA GGGTATTACA TGCATGAAGG TGTCAGATTG GGGGTTGGAT ACCAGAAAAT
10681 TACCTATGAC AACACTTGGG AATCTGCTTT CTTTTATTTT GATGAGACAA AACAGCAATT
10741 TGTATTAATT AACGATGCTG ATCATGATTC AGGAATGACG CAACAGGGGA TCGTGAAAAA
10801 TATCAAGAAA TACAAAGGAT TTTTGAATGT TTCTATCGCA ACGGGCTATT CCGCCCCGAT
10861 GGATTTCAAT AGTGCCAGCG CCCTCTATTA CTGGGAATGT TCTATTACAC CCCGATGATG
10921 TGCTTCCAGC GTTTGCTACA GGAAAAACAA TTCGACGAAG CCACACAATG GATAAACTAC
10981 GTCTATAATC CCGCCGGCTA TATCGTTAAC GGAGAAATCG CCCCCTGGAT CTGGAACTGC
11041 CGGCCGCTGG AAGAGACACT CCTGGAATGC CAATCCGTTG GATGCCATTG ATCCGGATGC
11101 CGTCGCACAA TATGACCCGA CACACTATAA AGTTGCCACC TTTATGCGCC TGTTGGATCA
11161 ACTTATTCTG CGCGGCGATA TGGCCTATCG CGAACTGACC CGCGATGCGT TGAATGAAGC
```

Fig.2.

```
11221  CAAGATGTGG TATGTGCGTG CTTTGGAATT GCTGGGTGAT GAGCCGGAGG ATTACGGCAG
11281  CCAACAGTGG GCCGCACCGT CTCTTTCCGT GGCGGGCAAC CACACTGTGC AAGCGGGCTA
11341  TCAACAAGAC CTTACGGCGC TAGACAACGG AGAAGGTTGC ACTCAACCCC GCAACGCTAA
11401  CTCGTTGGTG GTTTGGTCCT GCCGGAATAT AACCCGGAAT CAACCGATTA CTGGCAAACC
11461  TGCGTTTGCG CCTGGTTAAC CTGCGCCATA ATCCTTCCAT GACGGGCAAC CGTTATCGCT
11521  GGCGAATTAC GCGAGCCTAC GATCCGAAAG CGCTGCTCAC CAGTATGGTA CAGCCTTCTC
11581  AGGGCGGTAG TGCAGTGCTG CCCGGCACAT TGTCGTTATA CCGCTTCCCG GTGATGCTGG
11641  AGCGGGCCCG CAATCTGGTA GCGCAATTAA CCCAGTTCGG CACCTCTCTG CTCAGTATGG
11701  CAGAGCATGA TGATGCCGAT GAACTCACCA CGTTGCTACT ACAGCAGGGT ATGGAACTGG
11761  CGACACAGAG CATCCGTATT CAGCAACGAA CTGTCGATGA AGTGGATGCT GATATTGCTG
11821  TATTGGCAGA GAGCCGCCGC AGTGCACAAA ATCGTCTGGA AAAATACCAG CAGCTGTATG
11881  ACGAGGATAT CAACCACGGA GAACAGCGTG CGATGTCACT GTTTGATGCG GCGGCAGGTC
11941  AGTCTCTGGC CGGGCAGGCG CTCTCAGTAG CAGAAGGGGT GGCTGACTTA GTTCCAAACG
12001  TGTTCGGTTT CGCTTGTGGC GGCAGTCGTT GGGGGGCAGC ACTGCGTGCT TCCGCCTCCG
12061  TGATGTCGCT TTCTGCCACA GCTTCCCAAT ATTCCGCAGA CAAAATCAGC CGTTCGGAAG
12121  CCTACCGCCG CCGCCGTCAG GAGTGGGAAA TTCAGCGTGA TAATGCTGAC GGTGAAGTCA
12181  AACAAATGGA TGCCCAGCTG GAAAGCCTGA AAATACGCGG CGAAGCAGCA CAGATGCAGG
12241  TGGAATATCA GGAGACCCAG CAGGCCCATA CTCAGGCTCA GTTAGAGCTG TTACAGCGTA
12301  AATTCACAAA CAAAGCGCTT TACAGTTGGA TGCGCGGCAA GCTGAGTGCT ATCTATTACC
12361  AGTTCTTTGA CCTGACCCAG TCCTTCTGCC TGATGGCACA GGAAGCGCTG CGCCGCGAGC
12421  TGACCGACAA CGGTGTTACC TTTATCCGGG GTGGGGCCTG GAACGGTACG ACTGCGGGTT
12481  TGATGGCGGG TGAAACGTTG CTGCTGAATC TGGCAGAAAT GGAAAAAGTC TGGCTGGAGC
12541  GTGATGAGCG GGCACTGGAA GTGACCCGTA CCGTCTCGTT GGCACAGTTC TATCAGGCCT
12601  TATCATCAGA CAACTTTAAT CTGACCGAAA AACTCACGCA ATTCCTGCGT GAAGGGAAAG
12661  GCAACGTAGG AGCTTCCGGC AATGAATTAA AACTCAGTAA CCGCCAGATA GAAGCCTCAG
12721  TGCGATTGTC TGATTTGAAA ATTTTCAGCG ATACCCCGGA AAGCTTTGGC AATACCCGTC
12781  AGTTGAAACA AGTGAGTGTC ACCTTGCCGG CGCTGGTTGG TCCGTATGAA GATATCCGGG
12841  CGGTGCTGAA TTACGGCGGC AGCATCGTCA TGCCACGCGG TTGCAGTGCT ATTGCTCTCT
12901  CCCACGGCGT GAATGACAGT GGTCAATTTA TGCTGGATTT CAACGATTCC CGTTATCTGC
12961  CGTTTGAAGG TATTTCCGTG AATGACAGCG GTAGCCTGAC GTTGAGTTTC CCGGATGCGA
13021  CTGATCGACA GAAAGCGCTG CTGGAGAGCC TGAGCGATAT CATTCTGCAT ATCCGCTATA
13081  CCATTCGTTC TTAATTAAAA CATTGTGATA GGCAGGCTCC TGAGGGAGCC TGTTTAAGGA
13141  GTTTTTATGC AGGGTTCAAC ACCTTTGAAA CTTGAAATAC CGTCATTGCC CTCTGGGGGC
13201  GGATCACTAA AAGGAATGGG AGAAGCACTC AATGCCGTCG GAGCGGAAGG GGAGCGTCAT
13261  TTTCACTGCC CTTGCCGATC TCTGTCCGGC GTGGTCTGGT GCCGGTGCTA TCACTGAATT
13321  ACAGCAGTAC TGCTGGCAAT GGGTCATTCG GGATGGGGTG GCAATGTGGG GTTGGTTTTA
13381  TCAGCCTGCG TACCGCCAAG GGCGTTCCGC ACTATACGGG ACAAGATGAG TATCTCGGGC
13441  CGGATGGGGA AGTGTTGAGT ATTGTGCCGG ACAGCCAAGG GCAACCAGAG CAACGCACCG
13501  CAACCTCACT GTTGGGGACG GTTCTGACAC AGCCGCCTAC TGTTACCCGC TATCAGTCCC
13561  GCGTGGCAGA AAAAATCGTT CGTTTAGAAC ACTGGCAGCC ACAGCAGAGA CGTGAGGAAG
13621  AGACGTCTTT TTGGGTACTT TTTACTGCGG ATGGTTTAGT GCACCTATTC GGTAAGCATC
13681  ATCATGCACG TATTGCTGAC CCGCAGGATG AAACCAGAAT TGCCCGCTGG CTGATGGAGG
13741  AAACCGTCAC GCATACCGGG GAACATATTT ACTATCACTA TCGGGCAGAA GACGATCTTG
13801  ACTGTGATGA GCATGAACTT GCTCAGCATT CAGGTGTTAC GGCCCACCGT TATCCTGGCA
13861  AGTCCACTAT GGCAATACTC AGCCGGAAAC CGCTTTTTTC GCGGTAAAAT CAGGTATCCC
13921  TGTTGATAAT GACTGGTTGT TTCATCTGGT ATTTGATTAC GGTGAGCGCT TATCTTCGCT
13981  GAACTCCGTA CCCGAATTCA ATGTGTCAGA AAACAATGTG TCTGAAAACA ATGTGTCTGA
14041  AAAATGGCGT TGTCGTCCGG ACAGTTTCTC CCGCTATGAA TATGGGTTTG AAATTCGAAC
14101  CCGTCGCTTG TGTCGCCAAG TTCTGATGTT TCATCAGCTG AAAGCGCTGG CAGGGGAAAA
14161  GGTTGCAGAA GAAACACCGG CGCTGGTTTC CCGTCTTATT CTGGATTATG ACCTGAACAA
14221  CAAGGTTTCC TTGCTGCAAA CGGCCCGCAG ACTGGCCCAT GAAACGGACG GTACGCCAGT
14281  GATGATGTCC CCGCTGGAAA TGGATTATCA ACGTGTTAAT CATGGCGTGA ATCTGAACTG
14341  GCAGTCCATG CCGCAGTTAG AAAAAATGAA CACGTTGCAG CCATACCAAT TGGTTGATTT
14401  ATATGGAGAA GGAATTTCCG GCGTTACTTT ATCAGGATAC TCAGAAAGCC TGGTGGTACC
14461  GTGCTCCGGT ACGGGATATC ACTGCCGAAG GAACGAATGC GGTTACCTAT GAGGAGGCGA
14521  AACCACTGCC ACATATTCCG GCACAACAGG AAAGCGCGAT GTTGTTGGAC ATCAATGGTG
14581  ACGGGCGTCT GGATTGGGTG ATTACGGCAT CAGGGTTACG GGGCTACCAC ACCATGTCAC
14641  CGGAAGGTGA ATGGACACCC TTTATTCCAT TATCCGCTGT GCCAATGGAA TATTTCCATC
14701  CGCAGGCAAA ACTGGCTGAT ATTGATGGGG CTGGGCTGCC TGACTTAGCG CTTATCGGGC
14761  CAAATAGTGT ACGTGTCTGG TCAAATAATC CGGCAGGATG GGATCGCGCT CAGGATGTTA
14821  TTCATTTGTC AAATAAGCCA CTGCCGGTTC CCGGCAAAAA TAAGCGTCAT CTTGTCGCAT
14881  TCAGTGATAT GACAGGCTCC GGGCAATCAC ATCTGGTGGA AGTTACGGCA AATAGCGTGC
14941  GCTACTGGCC GAACCTGGGG CATGGAAAAT TTGGTGAGCC TCTGATGATA ACAGGCTTCC
15001  AAATTACGGG GAAACGTTTA ACCCCCACAG ACTGTATATG GTAGACCTAA ATGGCTCAGG
```

Fig.2.

```
15061 CACCACCCGA TTTTATTTAT GCCCGCAATA CTTACCTTGA ACTCTATGCC AATGAAAGCG
15121 GCAATCATTC TGCTGAACCT CAGCGTATTG ATCTGCCGGA TGGGGTACGT TTTGATGATA
15181 CTTGTCGGTT ACAAATAGCG GATACACAAG GATTAGGGAC TGCCAGCATT ATTTTGACGA
15241 TCCCCCATAT GAAGGTGCAG CACTGGCGAT TGGATATGAC CATATTCAAG CCTTGGCTGC
15301 TGAATGCCGT CAATAACAAT ATGGGAACAG AAACCACGCT GTATTATCGC AGCTCTGCCC
15361 AGTTCTGGCT GGATGAGAAA TTACAGGCTT CTGAATCCGG GATGACGGTG GTCAGCTACT
15421 TACCGTTCCC GGTGCATGTG TTGTGGCGCA CGGAAGTGCT GGATGAAATT TCCGGTAACC
15481 GATTGACCAG CCATTATCAT TACTCACATG GTGCCTGGGA TGGTCTGGAA CGGGAGTTTC
15541 GTGGTTTTGG GCGGGTGACG CAAACTGATA TTGATTCACG GGCGAGTGCG ACACAGGGGA
15601 CACATGCTGA ACCACCGGCA CCTTCGCGCA CGGTTAATTG GTACGGCACT GGCGTACGGG
15661 AAGTCGATAT TCTTCTGCCC ACGGAATATT GGCAGGGGGA TCAACAGGCA TTTCCCCATT
15721 TTACCCCACG CTTTACCCGT TATGACGAAA AATCCGGTGG TGATATGACG GTCACGCCGA
15781 GCGAACAGGA AGAATACTGG TTACATCGAG CCTTAAAAGG ACAACGTTTA CGCAGTGAGC
15841 TGTATGGGGA TGATGATTCT ATACTGGCCG GTACGCCTTA TTCAGTGGAT GAATCCCGCA
15901 CCCAAGTACG TTTGTTACCG GTGATGGTAT CGGACGTGCC TGCGGTACTG GTTTCGGTGG
15961 CCGAATCCCG CCAATACCGA TATGAAGGGG TTGTTACCGA TTCCACAGTG CAGCCAAAAG
16021 ATTGTCCTTA AATATGATGC GTTAGGATTT CCGCAGGACA ATCTTGAGAT TGCCTATTCG
16081 AGACGTCCAC AGCCTGAGTT CTCGCCTTAT CCGGATACCC TGCCCGAAAC ACTTTTCACC
16141 AGCAGTTTCG ACGAACAGCA GATGTTCCTT CGTCTGACAC GCCAGCGTTT TTCTTATCAC
16201 CATCTGAATC ATGATGATAA TACGTGGATC ACAGGGCTTA TGGATACCTC ACGCAGTGAC
16261 GCACGTATTT ATCAAGCCGA TAAAGTGCCG GACGGTGGAT TTTCCCTTGA ATGGTTTTCT
16321 GCCACAGGTG CAGGAGCATT GTTGTTGCCT GATGCCGCAG CCGATTATCT GGGACATCAG
16381 CGTGTAGCAT ATACCGGTCC AGAAGAGCAA CCCGCTATTC CTCCGCTGGT GGCATACATT
16441 GAAACCGCAG AGTTTGATGA ACGATCGTTG GCGGCTTTTG AGGAGGTGAT GGATGAGCAG
16501 GAGCTGACAA AACAGCTGAA TGATGCGGGC TGGAATACGG CAAAAGTGCC GTTCAGTGAA
16561 AAGACAGATT TCCATGTCTG GGTGGGACAA AAGGAATTTA CAGAATATGC CGGTGCAGAC
16621 GGATTCTATC GGCCATTGGT GCAACGGGAA ACCAAGCTTA CAGGTCAAAC GACAGTGACG
16681 TGGGATAGCC ATTACTGTGT TATCACCGCA ACAGAGGATG CGGCTGGCCT GCGTATGCAA
16741 GCGCATTACG ATTATCGATT TATGGTTGCG GATAACACCA CAGATATCAA TGATAACTAT
16801 CACACCGTGA CGTTTGATGC ACTGGGGACG GTAACCAGCT TCCGTTTCTG GGGGACTGAA
16861 AACGGTGAAA AACAAGGATA TACCCCTGCG GAAAATGAAA CTGTCCCCTT TATTGTCCCC
16921 ACAACGGTGG ATGATGCTCT GGCATTGAAA CCCGGCATAC CTGTTGCAGG GCTGATGGTT
16981 TATGCCCCTC TGAGCTGGAT GGTTCAGGCC AGCTTTTCTA ATGATGGGGA GCTTTATGGA
17041 GAGCTGAAAC CGGCTGGGAT CATCACTGAA GATGGTTATC TCCTGTCGCT TGCTTTTCGC
17101 CGCTGGCATC AAAATAACCC TGCCGCTGCC ATGCCAAAGC AAGTCAATTC ACAGAACCCA
17161 CCCCATGTAC TGAGTGTGAT CACCGACCGC TATGATGCCG ATCCGGAACA ACAATTACGT
17221 CAAACGTTTA CGTTTAGTGA TGGTTTTGGG CGAAACCTTA CAAACAGCCG TACGCCATGA
17281 AAGTGGTGAA GCCTGGGTAC CTGATGAGTA TGGAGCCAAT GTGGCTGAAA ATCAAGGCGC
17341 CCCTGAAACG GGCGATTACA AATTTCCCGT TGGGCAATTT CCCGGACGTA CAGAATATTA
17401 ACGGGAAAAG GCAAAGCCCC TGCGTTACGT TTCAAACCGT ATTCCTGAAA TAATTTGGGC
17461 AACTATGTCA AGTTGACCAA AAAATGCCCG GCAGGATATG TATGCCGATA CCCATTACTA
17521 TGATCCGTTG GGGCGTGAAT ATCAGGTTAT CACGCCAAAG GCGGGTTGCG TCGATCCTTA
17581 TTCACTCCCT GGTTTGTGGT GAATGAAGTT GAAAATGACA CTCCCGGTGA ATGACAGCAT
17641 AAAGCTCAGT GATGCCTGTT CACTGAACAG ACATCACTCC ATTTAGGAAT GAATCATGAA
17701 GAATTTCGTT CACAGCAATA CGCCATCCGT CACCGTACTG GACAACCGTG GTCAGACAGT
17761 ACGCGAAATA GCCTGGTATC GGCACCCCGA TACACCTCAG GTAACCGATG AACGCATCAC
17821 CGGTTATCAA TATGATGCTC AAGGATCTCT GACTCAGAGT ATTGATCCGC GATTTTATGA
17881 ACGCCAGCAG ACAGCGAGTG ACAAGAACGC CATTACACCC AATCTTATTC TCTTGTCATC
17941 ACTCAGTAAG AAGGCATTGC GTACGCAAAG TGTGGATGCC GGAACCCGTG TCGCCCTGCA
18001 TGATGTTGCC GGGCGTCCCG TTTTAGCTGT CAGCGCCAAT GGCGTTAGCC GAACGTTTCA
18061 GTATGAAAGT GATAACCTTC CGGGACGATT GCTAACGATT ACCGAGCAGG TAAAAGGAGA
18121 GAACGCCTGT ATCACGGAGC GATTGATTTG GTCAGGAAAT ACGCCGGCAG AAAAAGGCAA
18181 TAATTTGGCC GGCCAGTGCG TGGTCCATTA TGATCCCACC GGAATGAATC AAACCAACAG
18241 CATATTGTTA ACCAGCATAC CCTTGTCCAT CACACAGCAA TTAGTGAAAG ATGACAGCGA
18301 AGCCGATTGG CACGGTATGG ATGAATTTGG CTGGAAAAAC GCGCTGGCGC CGGAAAGCTT
18361 CACTTCTGTC AGCACAACGG ATGCTACCGG CACGGTATTA ACGAGTACAG ATGCTGCCGG
18421 AAACAAGCAA CGTATCGCCT ATGATGTGGC CGGTCTGCTT CAAGGCAGTT GGTTGGCGCT
18481 GAAGGGGAAA CAAGAACAAG TTATCGTGAA ATCCCTGACC TATTCGGCTG CCAGCCAGAA
18541 GCTACGGGAG GAACATGGTA ACGGGATAGT GACTACATAT ACCTATGAAC CCGAGACGCA
18601 ACGAGTTATT GGCATAAAAA CAGAACGTCC TTCCGGTCAT GCCGCTGGGG AGAAAATTTT
18661 ACAAAACCTG CGTTATGAAT ATGATCCTGT CGGAAATGTG CTGAAATCAA CTAATGATGC
18721 TGAAATTACC CGCTTTTGGC GCAACCAGAA AATTGTACCG GAAAATACTT ACACCTATGA
18781 CAGCCTGTAC CAGCTGGTTT CCGTCACTGG GCGTGAAATG GCGAATATTG GCCGACAAAA
18841 AAACCAGTTA CCCATCCCCG CTCTGATTGA TAACAATACT TATACGAATT ACTCTCGCAC
```

Fig.2.

```
18901 TTACGACTAT GATCGTGGGG GAATCTGACC AGAATCGCAT AATTCACGAT CACCGGTAAT
18961 AACTATACAA CGAACATGAC CGTTTCAGAT CACAGCAACC GGGCTGTACT GGAAGAGCTG
19021 GCGCAAGATC CCACTCAGGT GGATATGTTG TTCACCCCCG GCGGGCATCA GACCCGGCTT
19081 GTTCCCGGTC AGGATCTTTT CTGGACACCC CGTGACGAAT TGCAACAAGT GATATTGGTC
19141 AATAGGGAAA ATACGACGCC TGATCAGGAA TTCTACCGTT ATGATGCAGA CAGTCAGCGT
19201 GTCATTAAGA CTCATATTCA GAAGACAGGT AACAGTGAGC AAATACAGCG AACATTATAT
19261 TTGCCAGAGC TGGAATGGCG CACGACATAT AGCGGCAATA CATTAAAAGA GTTTTTGCAG
19321 GTCATCACTG TCGGTGAAGC GGGTCAGGCA CAAGTGCGGG TGCTGCATTG GGAAACAGGC
19381 AAACCGGCGG ATATCAGCAA TGATCAGCTG CGCTACAGTT ATGGCAACCT GATTGGCAGT
19441 AGCGGGCTGG AATTGGGACA GTGACGGGCA GATCATTAGT CAGGAAGAAT ATTACCCCTA
19501 TGGGGGAACC GCCGTGTGGG CACCCGAAAT CAGTCAGAAG CTGATTACAC AAGCCGGCGT
19561 TATTCTGGCA AAGAGCGGGA TGCAACAGGG TTGTATTACT ACGGCTATCG TTATTATCAA
19621 TCGTGGACAG GGCGATGGTT GAGTGTAGAT CCTGCCGGTG AGGCCGATGG TCTCAATTTG
19681 TTCCGAATGT GCAGGAATAA CCCCATCGTT TTTTCTGATT CTGATGGTCG TTTCCCCGGT
19741 CAGGGTGTCC TTGCCTGGAT AGGGAAAAAA GCGTATCGAA AGGCAGTCAA CATCACGACA
19801 GAACACCTGC TTGAACAAGG CGCTTCCTTT GATACGTTCT TGAAATTAAA CCGAGGATTG
19861 CGAACGTTTG TTTTGGGTGT GGGGGTACAA GTCTGGGGGT GAAGCGGCCA CGATTGCAGG
19921 AGCGTCGCCT TGGGGGATCG TCGGGGCTGC CATTGGTGGT TTTGTCTCCG GGGCGGTGAT
19981 GGGGTTTTTC GCGAACAACA TCTCAGAAAA AATTGGGGAA GTTTTAAGTT ATCTGACGCG
20041 TAAACGTTCT GCTCCTGTTC AGGTAGGCGC TTTTGTTGTC ACATCGCTTG TGACGTCTGC
20101 ACTATTTAAC AGCTCTTCGA CAGGTACCGC CATTTCCGCA GCAACAGCGG TCACCGTTGG
20161 AGGATTAATG GCTTTAGCCG GAGAACATAA CACGGGCATG GCTATCAGTA TTGCCACACC
20221 CGCCGGACAA AGTACGCTGG ATACGCTCAG GCCCGGTAAT GTCAGCGCGC CAGAGCGGTT
20281 AGGGCACTAT CAGGCGCAAT TATTGGCGGC ATATTACTTG GCCGCCATCA GGGAAGTTCT
20341 GAGCTGGGTG AACGGGCAGC GATTGGTGCT ATGTATGGTG CTCGATGGGG AAGGATCATT
20401 GGTAATCTAT GGGATGGCCC TTATCGGTTT ATCGGCAGGT TACTGCTCAG AAGAGGCATT
20461 AGCTCTGCCA TTTCCCACGC TGTCAGTTCC AGGAGCTGGT TTGGCCGAAT GATAGGAGAA
20521 AGTGTCGGGA GAAATATTTC TGAAGTATTA TTACCTTATA GCCGTACACC CGGTGAATGG
20581 GTTGGTGCAG CCATTGGCGG GACAGCCGCG GCCGCTCATC ATGCCGTTGG AGGGGAAGTT
20641 GCCAATGCCG CTAGCCGGGT TACCTGGAGC GGCTTTAAGC GGGCTTTTAA TAACTTCTTC
20701 TTTAACGCCT CTGCACGTCA TAATGAATCC GAAGCATAAC AATCATGTTC ATTCCCACTT
20761 TGTCATGGAT GACAAGGTGG GTTTTTCGGA TGTGTGGACA GAGACCCGTA CAGGGTCTCT
20821 GTCCAGTTAA TTTTTGGATC AAGAACGAAT GGTGTAACGG ATATGCAAAA TGATATCGCT
20881 CAGGCTGAGC AATAAGCTTT TCTGTTTACC ACTGATACCG GGAAAACTGA GGGTTAATGT
20941 GCCTGTATCG GCCACAGGAA GCCCTTCAAA TGGCAGGTAC TTAGCATCAT TGAAATCCAT
21001 CTGGAATTGA CCACTGTCAT TCATGCCATG TGAGATCACA ATCGCTTTGC AGCCACGTGG
21061 CATCATTGTA CTGCCGCCAT AACTCAGTAT TGCCCGGACA TCCTGATAAG GCCCTAAAAG
21121 GGCAGGTAAC GTCACACTGA TTTGTTTGAT ACGGCGTGTA TTACCTAAAC CGTCAGGATA
21181 ATCGGTAGCA ATATTCAGAT CCGATAATTT GAGGCTGGCT TGCAGTTGTG TCCCTTCGAC
21241 GTTCAAACCG TTAAGCGTTG TGCCTGCACT GCCTTCACCT GCATTGACTA ACTCAGTCAC
21301 TTTATCTTTT AAAATGAAAC TATTTTCTGT CAGACCAGCA TACACTTCAG CCAGAGAAAC
21361 GGTTCTGGTG ACCTCCAGTG CCCGTTCATC TTTTTCCAAA TAGCTTTTTT CCATCTGTGC
21421 TAAATTCAGC ATCAGGGTTT CACCCGCTAA TAAACCCGCA TAAGTCCCAT GCCAAGCACC
21481 TGGTTTAATA AAGTGTGCTG CCGCATTATT CAATTCATAC TGATAAGTTT GCTCTGCCAT
21541 TAAACAGAGT GAGACCGCCA AATCATAAAA CTGATAATAA ATAGCGGACA ACGTTCCACG
21601 GAGCCAGTTG TATAGCGCTG CATTACTGAA TTTACTTTGC AGAAAGGCTA ACTGCGCCTG
21661 AGTTTGTGCC TGCTGAGTTT CCAGATAGTT TTTTTGTAAT ACTGCCGCTT CACGACGTAC
21721 AGCCAGCGTC GCTAATTGAG CATCAATTTG TTTTATCTCA GCTTCCGCAT TATTGCGCTG
21781 AATTTCCCAC TCTTGCCGAC GGCGACGGTA TATTTCTGAT TGGCTGATTT TGTCTGCGGC
21841 AATACGTGTT GCTGACGCAG AAATTTCGAT ACCAATCGCA CTGGCATTGA AAAGCGCCCC
21901 AAAACGGGAA CCTCCCACAG CAAAACCGTA AATATTGGGG ACGAGATCTG CCGCGGCGGC
21961 GGCCATATGC AGGGCTGTGC CGCTGGTGCT CAAGACCGAT GAAGAGAGGT AAAGATCCAT
22021 CGCTTGTTTT TCACCAGCGT TAACATCTTC GTCGTACAGC GTATTGAAAC TGTCAAAACG
22081 AGACTGTGCA CCATGACGGC TTTCTTGAAG CGCCAATTTA TCAGCATCAA TTTCAGCCAT
22141 GACCTTATCC TGCATTTTAA TACTTTGCAG GGCTAACTCA CTGCCTTGAG TTTGCAGTAT
22201 TTCAGCCAAG GCTTCTGCAT CCTGCCGTTC AGTAATGCTG AGCAGGGTAT TGCCAAATTG
22261 TATCAACTGG CTTACCCCCC ACTTGGCATT TTCCAGAATC ACCGGAAAAC GGTACATCGG
22321 CATCACTGCA TGAGGTAAAT CGCCGCCGCC TTGTGAAGCA GTGATGGCAG CACTGAGTAA
22381 CATGGACGGA TCTGCGGGCG TGGCATAGAG AGATAATGAC AGTGGCTGAC CGTCGATTGT
22441 CAGGTTATGG CGTAAGTTAT AGAGGCGTTG CGTCAATGTC TGCCAGTAAC CTTGCAGTTT
22501 TTTATTAATT TGAGGGAGGA ACAATGCGGT TAACGAAATT TGCCGTACGT TTCGTGGGTA
22561 ATGCAGCGCG CTGACGCAGT TGCAGCATTT TATGTTGATA ATGATGCCGC ATTGTTTGGC
22621 TGGCAGCTTC TTCCAGCCGT GGCTCTGACC AATCGTTATC CAATGAAAAA TAAGGCTCAT
22681 CACCCAATAA AGTGAGCGCC TGTACATACC ACATTTAGC TTCGTTTAAG GTATCACGTT
```

Fig.2.

```
22741 CAAGCTGGCG ATAGGCGCTA TCTCCGCGGG TAATCAACAA ATCCAGCATT TTCATAAAGG
22801 TAGCCACTTT ATAGTGCATC GGATCATGCT GGGCAACGGC GTCCGGATCG ACCGAATCCA
22861 GCGGATTGGC ATTCCAGGAC GTATCTTCCT CCAATGGGCG GACGTTCCAG TAATAATCCT
22921 GCATTTCACC CTGAACCGAA TATCCGGTCG GGTTCAGATA TAGCGCAGCC AGCGTGTCGA
22981 TCCGGTAAAA TCTGCTCTTG CAATAAGCGC TGGAATACCA TCATGGGCGT TGTAATAGAA
23041 CAATCCCAAG AAATAGATTG CATTGGCGCC GTTTGAAATC CATGGGTTCA GTGTTATTTT
23101 TCATGACACG ACTTGAATAC CCCTTTTATA TTTTTTGATA TTTTTTACTA TCCCCTGTTG
23161 TGTCATTCCC GAATCATGAT CGGCATCATT AGTGAATATA AATTGATTTT TCGTCTCATC
23221 AAAATAAAAG AAAGCAGATT CCCAGGATTT GTCATAGATA ATTTTTTTGT ACCCAACCCC
23281 TAATCTGACA CCTTCACGTA TGTAATATCC TTTAGCATAG GGAACAAAGA GCGTTACTGT
23341 GGTTTCAATA TCAGATAACA TTCCTTCGTA ATAAGGTTGT CTGGCAGAAT TGCCATCAAT
23401 ATTCCCAATA TGGATCTTAA ACCAACGTTC ATCACCATGC TCCTCTTTAT TGTAGGGGGG
23461 CAACTTAAAT GTCGCATAAA ACCCTTCACC TAATTGCGGC TCTGGTAAAT TTTGCGTTTC
23521 CATACTTAAA ACATTATCAA TACCAATATT GGCTCTTTCA GCTAATTTTC TGGAAAATAA
23581 AGTATTTAAC CGGGTTCTGT AAGGGCCAAT CTGCATATAT TGTGTGCCTG ATGGCATTTT
23641 ATGCAGTGAT ATAACGTTAC TTGTATCTTT GGATTTTAGT TTTATATGAA TTGGCGATTC
23701 AATAACAATA TCGTTATAAC CGCCGTCGGG TTGCTTAATA ATAAACTCGC TCACCAGAGG
23761 AATATCATAG CCTTCAATAT CAACTTTTAC TTGATTAAAA TCATATACCA TAGGGTCAGA
23821 TTCGTGTGAA GGTTTAGATG CCACATGGTC TTCAGCATTT AACTCCACTA GAATATCAGA
23881 GCCATTTTTT AATAAAAAAC TAATGTTTTT ATCTTGGATC TGTTCGATCA TAGATGAAGC
23941 AAGTTTTATT ATCTGTGGCT GGTTGAACAT AAATACACCC ATGGATCCTC GCGAAGGAAC
24001 AGTGCCGCAA TATTTCCCAT GTTATTAATG ATTGAAACAT CATTAGTAAA TGATTCACAT
24061 ATAGTATGCC ATACTCCTGT GTTATCTTTC CAATCTAATA CTATGTTAGT ATCAAGTTTG
24121 AATTCAGCAT CATCTGATTC ATAATCATAA TTTATACCAA CTCCAATTTC TGATTTTCTA
24181 GGAATTTTTT CCTTGGTTCT TAGATGCATT AACACTCTAA AATATTCGGC ATTTTTAAGA
24241 TCGATGGAAA TAATAAAATC CAAAGTTCCA TAATGAAAAA CTTCTTCTTC TTTTCCAAGC
24301 ATTTCATCAT GTCTATCATA ATCAAATAAA ATAACCGTTT CATCTTCTAC CATCGATAAC
24361 AGGTATTTAA CCTCATCATT ATATATATTG CCTTTTGAAA AATTAATTTC CATTGAAGGA
24421 TTGAACGTTA AATTAATATG ACCATTTCCT GGTGATATAT ACGAGAGATC AAAAATATTT
24481 CCGGTAAAAC TGGCTAATTT ATTTTTTGTG GTTATAGATT CCTTATATTC GGCCAAATAA
24541 TCTGTAGCAA ATTGATTGTT GACTTTGTAT TCTGTCCTGG TATCAAGTTC TGATAATGTG
24601 CTCTTAACAA TGGCGTCTAA ATCATTTTCT GTGAGAATGG ATAATGTCAT ATCAGGGTTA
24661 ATGGTCATCC CTTCTCTTGC AGGAAGACTA TTAAAAGAAT AATTGTCTTT TTTCTCATGG
24721 AAATAAACAA TAATGACGTC TTTTTCATAA TCAGAAGAAC AATACATACC AATGCTGGCT
24781 TTTTTATTGA TCAGGTTTTC TATTTTATCA GTCACATTAA AATTAAACGG TGAGCTCCAG
24841 CTGCCATCAT AACGAATATG TGACAGTTTT AATATATAAT CAGTGATATC TATCTTGCCA
24901 TCTTCACTTT CATTTTTCAG CTCTTTTTGT TCCAGCCACA GTAAATACAA ACGAGACTTG
24961 TAAATAACAG GTCTGATATT TTCCTGCCAT ACATTGATGG GTATTTCAAT TTTTTTCCAT
25021 TCTCCCCAGG CATTGGCAGC AAATTGACCG TGCTGGCACT TTTGGTGATC GACATTGCGC
25081 CAATAATATA TTCTGGGTTC TGTCTGGCTA TAACCAATTA AATAAGTGAG CCCCTCATTG
25141 ACATTAATAC TGTCATGATA TCCGCTAATC ACCTGCAAGT TAGCGACATC TTCAAATGCG
25201 GTCAGATAAT TTTTAAAGCT ATCTTCAACG GTATCGATAT TTAACTGACT TTGGGAAAGT
25261 TGCTGTAACA GGTTGTTCAT CATACCTGTC TGACCAATAC GAATCGTGGG GTCGATATAG
25321 TTTTCCGGAT AATAGGCCAG TTCAGATACG CCGGCCCAGG TGCTATACCG TCGATTGTAG
25381 GTTTCCCAGT CGCAGAAGAA CTGACGGGTT TTCACTGGCT TTGATACTTT TCCTTCAACA
25441 TTATTCAACG CCCGGTTGAC ATATAACTGA ATGCTGGCAA TGGCTTCTGC CACACGGGTG
25501 GTTTTCACTT GGGCAGAAAC TTGGTTATCA ATCAGCAGAT AGCTGTACAA CTCATCCCGG
25561 CTCTTAATCT GTTGAGGTGC ACCATTTTTG ATGTAGTAAG CACTGGCCGC TGTCGTCGTG
25621 GCTTCATCCA GCCATGCCTG AAGCTGGTCG GATTGTTGAC TGTTCAGTCC CGCCTGCAAC
25681 AAAGTACTGG CGGCTTGCCA ATCATCAAAT GTTGGCATCG GGGTTTCCGG TTCACCGACA
25741 TATTTTAATT TTATGAGTGC AGCAACACCA TCCGGGGTAA TACCCAATGT AGCAGCGACA
25801 TCCAGCCATT GCAGAGTGAC ATCTATAAGT TCTCCAGTTG GTAAAGGTAT TCACTCCCAA
25861 ACCGGTCTGT TGCAATGCTT GTGTCACAAC CTGAGCATCA AAATTTTAAC GCCACCGCCA
25921 AATTGTTCGG CAGTCAACGC TCCTAAGTTC CAAATGCTGT TAAGATTCTG TCGCGTAGCT
25981 TCACAACGCA TGATCACAGC ATGGAAGCGG GTCAGCGCTT GCAAAGTGGG GAGATCATGT
26041 TGCAGTGCTG TGGTTTCTGA TTGGAATTTC TCCGGTTTTG TCACCAACAG GGTCAGTTCG
26101 TTTTCGCTGA GTCCAATATT GCGCACAATC AGAGAAAGTT GCCCCAGTAC CTGACAAAAA
26161 GCCACCATGT TGCTGGTTTC ATTCTCTGAG CGATCACGGT TAGCCGCAAT AATCATGAAA
26221 TCATCGAATG TCAGTCCTTG TGGTTTTATC TGATTAATCC ACAGCAAAAT AGTTTCTGCT
26281 GTTTTGGCTG AATCCATTTG AATGCTGGCA GCAATCAGCG GGGCAGCTGC ACGGATCAGT
26341 TCGTCATCAC CGAGTGAAAG TGTTGATAAT CCATTACTTA GTGTCGTGAT AAGGTTTTCA
26401 ATATCCGGCG TAAGGACAGT GCTGTAATTA TCCGTGGTCA TCAGAAACAC ATCACTGACA
26461 GACCATTTCT GTGTTGTCAG CCACTGGGTG CATTGGAACA GAAAGCTGAT TAATTGCGTT
26521 AATGCTGTAT CAGAAAAAAG GGCAATTTTC GTGTTCACAT AGGGAGAAAC CGACAACAAC
```

Fig.2.

```
26581 ATGGATAATT CATTCACTGT CAGATGATGA ATGTCTGCCA GCAGACGAAC GCGATAAAGC
26641 AGAGACAGGT TCTCGATGGA ACACATAAAT TCTGGATTTG TTCCGCCATT AGCCAGTTTC
26701 CATAATGTAT ACAGTTCAGT ATCATTCACT CTGAAAGCAC GTTTCATTAT TCCCAAATAA
26761 AAATGGTTTT TTGATTCACC GGGGGTTAAA TCCAGTTTGG TATTATCAGC AGAAAACTCT
26821 TGGCCATTTA ATAGCGGTGT ATTGAACAGC ATTGTAAAAT GACTGGGTTG TTGTTTAGTG
26881 GAATATTGGC TGATATCTGA ATGACACAAT ACCAGCGCAT CGCTGACGCT AATATTATAG
26941 TGCTGCATAT AATATTGAAC ATAAAACAGC TTACCCAACA CATTGCTGTC AATGGTTAAG
27001 TCATCATAAA TACTTTCTAT TACTTGCCAG ATATCTTCTG GAGATATGCC TGTGGCTTTA
27061 TACAAACGAA TCGCTTTATT CAGCTTTAAC AGGAATATAT CACCGGGAAC TCCATCATTT
27121 TAAAGTGTGC ATTGGCATTG ATAGCATCCG ACGGATTTGG TTAACTCGCC ATAAGCGGAG
27181 TGTTATACCG TTGGTGATTT GCTCTGTCGT CAATTTAATG GGAATACTGT AATGGGTATT
27241 AGCAATGGGG ACGAAATTTT TATCTTGGTA TATATATTCT TTATCTCCAT TCTGGAGACG
27301 AAAATCCAAG TGGTCAGGTT CTGTTTTTTT TACACTGAAA TTATATTTGT ATTCATTTTC
27361 TTTGATTGGA ATTAGCTCTG CATAGTTTAA ATGTGAATCG TAGAAATCTT TGCGGGTTCG
27421 CTTAATCAAT CTTGCCGTTG CCGTATCATT CCCGTCATTG ACCAATGTTA TCAGTTGCTC
27481 ATTCTTATAC TGTTGATTTG TATTTTTCTT ACCGAAGGAG AGATTGACAA ATAAACTGAG
27541 TTCATCATAA GACAAATCGT AGTAGCGAGC CAAAGAAGCA TAACTCTTAA AAATCAGTAC
27601 ATCATCTGTA CCGAAATTTT TCTTCATCAG TTCTGTTGAA TTTTCCGGTG TAATTTCTTC
27661 TACAAGGATT TGATACAATT CAGGCGATAT ATCAGTCTTA ATAGCCAGTA GCGATGTTGG
27721 GTCCATTAAT TCCGCTACGT CTGTATTACG GCTAAATGCG GTGAGGTTTT TATCTTGCAA
27781 TAAAATTGCC TGACGGGCTG ACTCATACGG CAGATGATAG GGTGTCATGC CGGTTTGCCG
27841 GTAAGTGGAC AACATTTTCA TTACACCGTT ATAGTCAGTT TTCTCTAACG TCTGAATATT
27901 ATGCAGCAGT AATTCATTAG ATAAGGATAA TGTGGAAATT TCTTCATCCA TATTATTCTG
27961 TGTCAGTGCC AGTGAAGCAA TGTCGGGGCG TCGTTTATTC AGGTGATATT GAGAATTGTC
28021 AGGATGAAAA TCTTTCGCTT CCCGATATAA TTCTGTTAAA TAAGCCGCTG GTGAAAATAT
28081 GGAAGCAATT GATCCCGGTT TTACAAAACG GTGGGCGCGG CCATAAAACC AACTGTTGTA
28141 ACTATTGTTT AGGGTTGACG GTGTAATATT AAGGTTAGTG ATATTAGCCA GTTGTGGATT
28201 AGCACGGGAC AAAATGCGCA GTTCTTCAAG TTTATTCTGT TTTGATTCCT GATGAGCCTG
28261 TTGATATAAA AAGTCTGTTT CTCGCCACGT CAGAGTTCCA CTTGTCCTAT GACGAAATTC
28321 GCTGAAAGAC ATAAACGAAA TGTTTGTCAA TAATAAAGTA TCACCAGCCT TTTTCTATTT
28381 ATCTTATCTA ACAGTTCATT AACTTTTATC ATATAAATCC TTAAGTTATT GTCAATTTAA
28441 TGATTAATGG TTTTTAGGTG GAGATTATTA TAATCTGATA GGAATATTAT GGTTAATTAA
28501 ATTGATACTG ATTTATCGCT CTATTCTTTC AATAAAAAAT AAAGAACTTC CCTATAATAC
28561 ATGGATTTAA ATAATGAATA CCGTATGTTA AAAATTAAAT TTTAACAAAC TTTCATGAAA
28621 AAATTCAACT CAACAATTGT TTAAATATTT TTAATTGTGT TTGTGCTGTT TGAAAAATGA
28681 ATGACTAATA TTTATCTATG AAAGATTATT TATTGAGGAT GTCTTGCTTG GTTTCAGGGG
28741 GCTACGTTGG AGTCAGATAA ATGTGTGCAA AAAGAAATCC TTAATAAAGT TGCGTAATTA
28801 CAAAAGTTGG TATATCGTGA CAAGAGTGAT AGTAATGTCA CATAATTTAT TGAATACCCG
28861 AACCTCGCAA ATGCGGGGTT TTTCTTCGCA TAATCAAAGA GAAAGCTATG AAAAAAACAC
28921 TGATTACTCT TATTCTCAGT ACCCTTTCTT TTGGTGCTTT GGCACAGCAG GGTGGCTTCG
28981 TTTCCCCGGA CAGCACAGAC TATACTCAGG GTGGATTTAA AGGTCCAACT CCCAACCTGA
29041 CCAGCGTTGC TCAAGCAAAA TCTTTTCGTG ATGATGCGTG GGTTGTTCTG GAAGGAAACA
29101 TTGTTAAACA GGTTGGTCAC GAACTCTATG AATTCGCGGC CGCATAATAC GACTCACTAT
29161 AGGGATCGCT TATTACGGAC TTATCCGGAA AGCTATCTGG AACCCCTGTT ACGCCTGAAT
29221 AAAACAGAAT TCAGGGATAA CAGTGGTTCT GTTTATGTTG ACATTGATGA TAAGCGCTGG
29281 ATGGGTCTGA CGGCCACTCC AACTGACAAA GTTCGTATCG AAGGTGAAGT GGACAAAGAC
29341 TGGAACAGTG TTGAAATTGA TGTCAAAACT ATCCGCATAG TGAAATAACT CAAGCACTTT
29401 GAATATAGCC CCGCACTCGC GGGGTTTTTT GCTTTCTGGG AGTCGGAAGT TTAACCGTAG
29461 TGACGAGGAT CAAAACTAAG TTAACGGCAG TGGTCACTGA TTTGGTGCAT AAGTTATCAA
29521 AAGTTAAAAA TCAAAACTTA TTTTTTATTT AATAGAGGAA TGTCACCCTG TAGGTGAATA
29581 ACGTTGACGG ATGTAAATAT ACAGTATTAT AGTCCTTTGA TATGTTATTA AATTGAAAAA
29641 CCTTTAAACT ATATTCGGGG GAAATTATTA TGTCAGATGT TCGTAATATT ATTAATGTTG
29701 ATAACAATTT TGGTTGTGAA TATAAAGCGG ATTTATTTAA ATAAGTTTTC ATAATTGTGA
29761 TACACCCATT TTTCTCATCC CCGGTTTTTG CTGTTGTAAG GAAGCGGTTT CCATGAAGAT
29821 TTTGACATGG TTAAGCAACT GCCACATAAA TTGGCAGCAG TGGTTTCGTG TCACGGTTTC
29881 ATGCAAGGAT TGCCATAGAC GTTCAATTTT ATTCAACCAC GGGCAATAGG TCGGTAAAAA
29941 GAGAAGATTA AATTTGGGAT TCTTTGCCAG CCAAACCCTG ACCTTCCGGC TCTTATGAAT
30001 GCAATAGTTA TCTAAAATTA ACGTGATGGT TTTGGCATTA ACATATTGAT TGTTAATTTC
30061 ATCTAACAAT TTGATAAATA AATCTGAGTT CTTTCTCAAG CTACCGACAT AAGTGATTTC
30121 TTTCGTTTTC GCGTTGAGGC AATTGGCAAG GTAGTGTTTT TGGTTCTTTC CGGGGGTAAC
30181 AACACGCTTT TGTTGCCCTT TGAAGCACCA GTCTGCACCG ATTTTCGGGT TCAGGTTGAT
30241 GTCCACCTCA TCCTCATAGA AGACCGGGTG TTTCTCTTGA GGCATTGGAT AACGTCTCGC
30301 TGATTTTTGC CATTTTTTCA TCATACTCAG GGTCAGGCAA TTTTACGGTT GGTGCCGCCC
30361 TTCGCCAAAC GATGCCCGTC CGGCAAAAGT AGCGATAGAG GGTACTTTGA GAGAGCGATG
```

Fig.2.

```
30421 TATTCAGTAG CTCATTGATT TTAAGTGTAA TAAGCTCAAG GCTCCATCGT GAACGGAGAT
30481 AGCCAAAATG TTGTGGCGAG TGCTGTAATA AGAAAGAAAT GACTGTGAAG AGCGGAGCTA
30541 AGTTCCAGAT GGCAGGCCTT CCCGCCGGGA GGCTTTTAAG TCCTTCCAAC CCGTATAATG
30601 TTAACCAATT TACCCAACGA TGAACGGAAG AACGTGAACA GTGAAGCGTT CTGGAAACGT
30661 GAGAAACCGT ACTCCCTTCA TGTAACATCA AGAGCGCGGT GAAGCGACGT GCATAGTCCT
30721 TATCCCGGGT TTTCTGGATA GCTTTTTTCA TCGGACGTCG TTCATTTCGG GGTATTGATG
30781 TTATGATTGG CATGACTCAG TCCATTTTGG GATTTGTTTT GATTTGGCGA TTAATCAGAT
30841 CGCGAAAATC GGACTGAGTT CCCTTCAAGT GATCTACTAT TTTGAAATCT TATTTAATCA
30901 GGAGTCAGCA AATGAGTTAT TCCCCATAAT ACCTGACCAT GTGGTTGTTT ATCCGGGAAA
30961 TGATTCATCT ACCGGTGGTA TGTGGATTCC TTGGTGCGAT AGTCAGAAAG ATATTGACTC
31021 TGGCCATTAT ATCAAAGTTA CTTTCAGTAA AAAGGACGCT GCTGATATTG TGAACTACAT
31081 GTTTCAACAT GGCAGTTATG TTTATTTTAC AGACAGTAGT AAACAATTTA GCAATAAGCA
31141 AATTATGTCT GGTGATTCAG CTAAAGGCAA AGGGGATTAT AAGCTTGAAA TTAAAACAAA
31201 CGGGAACCTT CCACTGATGG TATTGAATAA ATATTGATTC ATTATTATTT ATGGATAAGA
31261 AATTAAGTTT ATATTTCATC TGGTTTCTGC AATTAAGTTT TAAAAATTAA TTCTACTTTT
31321 TTTATGGTTT TATATTTAAT GCCAATCATA TTATTTTTCT TATAATAATT GATAGTTTAT
31381 TTATATAGTA AATAAATTCT GTTGGATGTG ATTATTATTG TGAGACGGTA ATAATTAACA
31441 TAACAGAAAA TTCATGGTTA GGAAATTCAA TCAACTTTTG TCCGGTTTCC TGACCATGAA
31501 GAGCTGTATT TACTGTAGAA CTCGCATTGA TACTGGATTG ATTAGCCGGA CGAGTGTTGG
31561 GTCAGCAGAT AATATGTTGT ATATTGGCTG TGGATTTTTC AGCGAGATGA TAGCTTTGGC
31621 AGTAAAGGCG ATTAATAACC GATAAAACAG AGAGACGGAT TGTGGCCAGG AAAGCAAAAA
31681 AGCCTCACCA TGACGCGTTA TTCAAACATT TTTTAACCCA ACCAGAAACC GCCCGGGAAT
31741 TTTTATCCCT TTATCTGCCG GAAGCGATCC GGTCAGTGTG TGATTTACCA CACTAAAACT
31801 GGAACCGGCA GCTTTGTGGA CAGGCAATTA CGTCAGTTGC ACAGTGATGT GCTGTATTCT
31861 GTCGAGACAA CCCACGGGGA CGGTTACATT TATTGCCTGA TTGAACACCA GTCCACGCCT
31921 GATCCGTTAA TGGCCTGGCG GCTGATGTAT TATTCGCTGT CAGCCATGGC TGCGCATCTG
31981 AAAAAAGGAC ATACTGAACT CCCTTTGGTC GTCCCCCTGC TGTTTTATCA TGGTGAGGTG
32041 AGGCCTTACC CTTACTCAAA TCGATGGCTG GATTGTTTTA CACTCTCTGA ACACGCGGCT
32101 CACCTGTATA ATCAGCCCCT GCCGTTGGTG GATATCAGTG CGCTCAGTGA TGAAGAGATC
32161 CTGACACATA AAAGCATTGC CTTGATGGAG CTGGTACAAA AACATATCCG TTGCCGGGAT
32221 ATGCTGGAGT GGGTTCCCCA ATTGGTGGCG TTGTTGAATG CCGGTTATAA TAGCGCCGAA
32281 CAGCGCCATG TTGTGTTAAG CTATATTTTA CTGAATGGAC ATACGCTGGA TCTCGCCCAG
32341 TTTGTCCATC AACTGACTGA ACAATCTCCG GAGCATGAAA CCATGTTGAT GACTATTGCA
32401 GAACAGCTTG AACAAAAAGG GCGTGAGCAA GGCCGGACAG AAGGCAGAAC AGAAGGCAGA
32461 GCTGAAGGAC GGGAAGAAGG CAAGCTGGAA ACGGCGCGCG CATTATTACG GCATGGTGTC
32521 AGTCTGGACA TCATTGTCAC CAGTACCGGC CTGAGCCGGG AGAAAATTGA AGCGTTAAAG
32581 CATTAAATGG ATACGCTTTT TCACAGCAGG ATATGGTGAC CCCTGTGAGG CCACCGGAAA
32641 ATTTTATTTA CTACGATTTA CGACGGGTTA CTTTAGGAAG CTGAATGAGA CGTCCTTTGT
32701 TATATAACGG TCCCATATCA ATCTTCTCTT TTCCGCGTAC AGGTAAGTAA CCCAAACCTT
32761 CGTGAGCAGC ATTTGCCAAC AGGCCATCAT CCTGATCGCC TGACCAAGAG AAGATCCCGC
32821 CCAATTTCAT TTTGGTTGCA TAAATTCCCT TATGCAGCAC AGTGCGGGGC GTATCCAGTG
32881 AAATCCAGTG ACCACCGTCA GCATTAAAGA GTGCGTCAGC GTCGGTTTCC GTGTCTGTCA
32941 CCAGTTCAAA CTGATTTTTC CCGCGTGCAA TTTCATATTC CGCATCGTAT TGGTTATTCA
33001 GCAGACAGAA GAATTCCGGA GCACCTTTTT CCATCGTGCC CAGTGGCTCT CCTGTTCTGT
33061 TATAGCGGCG CGTTGTCAGA TCAGCACCCA GACATGAACG TCCATAGTTA GCAAATCCGA
33121 GGTGAATTTT CTCCGGTTGT ACACCTTGTG ACAGTAAAAA GCGGATCGCC TCATCTGCCG
33181 AGTAATCCAT GTCCCGATCA GGATTGGGCG GAGGAGGGTT ATCGCCGTCA TATTCATATC
33241 TGGGGGGATA CAGGTTAGTA TGGTGACCGA TGTATTCTGC CCAACCGGTA CCAAAGAAGT
33301 CGTAGGTCAT CACAAAGATA TTGTCTAAAT AAGGTGCGAT TTCTTTGAAG CTGGACTTCT
33361 CCATTTTGGC AACGACGGCG CTACAGGCTA TCGTGATTTC TTTACGGGCC CGGGTTCCAA
33421 AGGCGATGTT CAGTGCTTCA CGCAGCTCTT TCACTAACAA AACATAGTTT GGGCCATCAT
33481 GTTCCGGGTC GAATTCATTA CCTTCTTCAC CTGTGGCGCC GGGGTATTCC CAGTCGATAT
33541 CCACCGCAGT AAACATGGGA AAACGCCGGG AAGAAGTCGA CGATGCTACT CACAAATGTA
33601 GCACGTTGCT CAGGATCTTT GGCCATCACA GAGAAATACC CTGACATACT CCAGCCGCCG
33661 ATACTGAATG CGAGTTCCAG CTTATGCCCT GCCTGTTTTG CTCGCGCTTT CAGATTACGC
33721 AATCCCCCCA GTAAACCGGA GGCTGCATCC TGATTGTAAT ATTGCAAGAA ATTCTTCGGG
33781 CTGGCATCAC GGCGCTGATC CGCGTCCAGA CCGACATTGC GTGTGGTGCC TAAATCACCA
33841 TAAGGATCAA CGGGTACAAT ATGGCCTAAT GTAATAGGGG CAATCTGGCC ACTGCTGGCT
33901 TCTGCTTGCC GGTTCCACCC GTCAACAACC TCATTAATCC GTTCGGATAA CTTGCCTTTG
33961 TCACCGTTGA CGGCCATAAA ACTGAAAATC AGGCGGTCGT AGGCGGTAGG CGGGATTTTT
34021 TCCAGATCAA AACCACGGCC GGGGGCATCG TCGCTGGTCA GCGCAGTGTT ATCCTGGGTT
34081 TCTGGCGACA AACGCGCATC ATACTGGCAC CAGTCAGTAA TATAGGCAGA GACTTTAGGC
34141 AGCGGTTCTG TATTTTCCGG ATCAACTTCA TATTCGTTGT ACAGGGACTT GGCAACACGT
34201 GCTGAAGAAT AACTCAAAGG AGTTCCGCTG CCGTCAGGTT TATATCCCAC CTTCTGATAG
```

Fig.2.

```
34261 GTTTCTTCTG TGAGTGCATC ATATTGCAAT ACCTCGGTTT TTTCTCCCGG CGGTACATCA
34321 GGCGTATTGG GGTTACCGTG ATCGGCAATT TCTTCCGGTG TCGCCTCACG GACATATTGC
34381 CAGGCATTCT CATAAACCGG TAAATCAGGT GAAATATTGC GGTCGGGAAT ATGCCAGCGT
34441 TCAACCCAGC CGATGTTTTT AAAAACCGCG CTATCATAAA TGACATACCA GGTTTGACCA
34501 CCAGATTGAT TCTGCCAGGC AACCAGAGAT GCGCCTACTT CGCTGCTGGC GTCAGACATC
34561 GCTTTAATTG AAGGGTATCG ATAAACATTT TGAGACATAA TTTCACTTCC GGCCCCGTTA
34621 TATTCCGGGG CCGGCTCCTG ATATCAGTTA GAATTGTCTT GTTTTAATTG ATGTTTATTC
34681 AGACGGCTAC GAACCTGCTG GCTGAACTCA TTACTTCCGC CACTCACATC ACGCGCGGTA
34741 TAACGCAGAT GGAGGATAAT ATCGCTCAGC GACTCCAGCA GCTGATCCTG ATCGGAACCG
34801 AATTCCAACT TCCACTGTGA AATGGCGCCT GTCCCTTCAA AAGGCAGGAA AAGTTCATCA
34861 TCAAAATTGA GCCTGAACAT GCCGCTGTCT TCCATGGCCG TTGAAATCAC CACACCTTGA
34921 TTAGCCTGTA CGTTCAGCAA AACGTTTTCG GGTTTGGTGT ATTCCAAGGG GTTAAGCAAA
34981 TAATCGATAG TTTTTAAGTC AGCAGTACTG TAAAGCGTAT TGCTGAGTTG TACCAGTGAA
35041 GCCCGTACAT CTTCATAAGG CCCCAGCAAT GCGGGCAATG ACAGCGCTAC GGTTTTTATA
35101 CGCCGATCAG CGTGGGTCGG ATAATCGCGC AAGAACATTT CGGCGCTCAG TAAGAAAGTG
35161 AATGAACCCG TACTCTTGCC AATTTCCCAC TGTGATGATG TCAGTAATGA TTTTACCGAT
35221 ATGGTTTTTA TGATCTCCAG ACGTCTGGTG TTATGTTGCA AATACGCCTG ATCCATCCGT
35281 TGTAAGGCTA ATTTCAGATG TTCTCCGACC AGCAGCCCCT GATAAAGATC ATTCCAGAGA
35341 CCACTTTGGA CGAAATTCAT ATCATACTGA CCTGTTTCGT ACTGCCAGGA GGCTTCGGCC
35401 AGTAAACAGA GGGAATTAAC CGCATCATAG GCTTGCAGGT AAAGCCGGAG ATTTGGCTGA
35461 TCATCCACAT GTATAACGCA TCATTGGTAN ANTTGTTCNN NNNNNNNNNN NNNNNNNNNC
35521 CCGAAGCATA CCGCCAAGAC CATCCCCCCG ACGGCCAGAC CGAAAATATT GGGAACCATA
35581 TCCGCCACAG CGGCCGCAGT GGCGGCTGAC TGGGCAGCGA TCACACCTTC AGCCGCTCTT
35641 GATTGTAATG CGATAACTTC CTGCTCGGTG ATGGAGATGT TTTCATCATA GAGCGATTTA
35701 TAGTGTTGCT GGCGCTCCTG AGCGGCCCGT CGGCTGATGG TCAGTGCATC CAATGAAGCC
35761 TGTTGCATGT CAATCGCTTG CTGTTGCAGA TTGCGGGTAA AGCTGTACAG CCCCAGTTGC
35821 TGCTGCATAC GGAAGTGTTC AAAATCGGTA TTGTCTTTTT TCTCCAGCAA ACTCAGTAAC
35881 GTGCTGCCGT ACTGAATCAG CGTTTCTGCG GCCTCTTTTG CCCGGCTCAT GATCGGGGTG
35941 AAACGATAAT TCGGGATTGC CCGGCGTTTC ATGCCCGCCA TACGATTAGC CACAACACGC
36001 TGGTAACGCT GCCTGAGCAG ATCTTGCGGG CTGATGGGTT CATCGTATAA TCCGGCCGGA
36061 AACTCTTTAC CATCCAAGGT CAGGTTATGA CGTAAGTTAT ATAGACGCTG ATCCAACATT
36121 TGCCACAGTT TGAGATATTC CGTATCAACA GGTTTGACAA ATAAATCAGA CGGTGCGGCA
36181 GAGACGGATG TATCATATGT CACAGGCAGA AGTGGCACGT TGCTGACAGT AAGCATTAAC
36241 TCCTGTGCCC GTGCTTCACT GTTTTCATAC AGAGCCACAT CTTGCAGCGT ACGGGGTTGC
36301 CAGTTTGCCG CGAGCAGAAT ATCAGGGCTG GTACCCAGTA ACATATTGAC GGAGTCATAG
36361 ATCTGCTTGG CGACAGTACG TGCACTGGAT GTCAGCTTAC GGTATTCCAT GTCTCCCTGA
36421 TCTAACAGAT TCTTGACATA GAAACGGAAT ATTGCTTTCC GGTAGTGAAT GGGTTCACTG
36481 GCTGCAATGG CATCCGGATC GGTTGGTTCA ATTAACATCC GGTACACGGT GGGTGGAGGA
36541 TCAATAATTG GCCGTGAATT CCAGTAACGC GGTTTACCTT GGTTGCTGGC CTGAACAAGT
36601 TCATCTTCCA GCGGATTAAA AATATAGTGC AGCCATTCGG TGGCCTCTTT TAATCGTTGT
36661 TCTATATTCA GTCGCCACGC GACCAGAAAT GGCATATGGA AAAACAGTTC CCAGAAATAG
36721 ATCCCATTTG CGCCATTTAA ATCAATCGGC GTAGGGAATG AACCGGGTAT AGGCTGTTCG
36781 GTAATAAGCT GTGTATTCCA GCTCAGTACC TGCGGGATAC CCTGACTGGC AATGGCGATC
36841 AGTTTTTTTG CAAACAGTGT ATTAAGGCGA ATGTTTTGTG GCGCGTTATC AGTTTCATCT
36901 GCGGGGAAGG AAAGGAATTG CACCTGATCC TGTTCATTGA GTTTAATCAG TTCGCGAATA
36961 TGCATACCGA TTCTGAACTC TTGAGTACAG CTGGCACTTT CATTGCCAAC ACCACCTTTG
37021 GGCTTAAAGA GAAGTTCGGC TTTCAGGGTG ATTCGATTAT CCGACCCCAG CTTGATTGAT
37081 GGATAGGTTA AATCAAGAAC TTTTTCGCTC AGTACCAGTG GTTGTTCATC CAAGACAGTA
37141 TTATCGTGCA TCAGCCGGAA AGAACCGTTG TAATATTGAT GATCTTCTAT CGCACCAAAC
37201 TTAAAGTCAG ATTGAGCGAC AATCTCCAGT GTGTCATCAG TGCCATGAAC AAAATTGACA
37261 ATCAGTTTGA TACTGTCTTT GCCGAAATCA GGGTTCATTC CGGTTTGGAT TCTCCGGCAA
37321 TAGGAAAGCG TTCTTCCCGG GTTGCCGGAT AGAGCACCAT AGTACGGTAA TCGATAGGAT
37381 TGCCTTAAGG CATCCTTGTG TTCACGTGAG TAATACCAGA CCAGGTTGCC GACATATTTT
37441 CCTTTTCGTC CATCAGCATA TTGGTCATCC GGCAAATCAG TAATTTCTAC CAGCAGTGTA
37501 TCGCAGACAT AACCGAAGGC TTCGTCATAA TCATAATCCT TACCTTTCTT ATCTGTCCCC
37561 TGAAGACGGA CAAACGGAAC CAGAGCCAGA AACGGGTTAT GCGGGTCTTG CTGTATATCC
37621 ATCACAGCAA CCATCTGGGC CATCCGGTAT TGCAGATGTC TTCGCGCAGA ATGGTGGGTG
37681 TACTCCAGCT GCCATCATAT TTGGCATAAG CGATTTTGAT CCGGTCAGGA ACGGTGTGGG
37741 AGGAACCCAA TCACCCGCAC TAGGCTCAAC GTTTTGGTTA TGCAGTGATA ACGCAGTTGT
37801 ATCTTTAGTT TCAGACTGTT CTTCAACTTC CGTCCAGGCA ATATACAGGC GATTATTCAG
37861 GAAAATGGGG CGTATCAAAT TGGGGTCTAC GCTGCCCAAT GGCAGGTCAA TAGGTTTCCA
37921 CTCGCTCCAG GCATTGGGAG ATAACGCATC GGTATCAGGA TGGCGTATCG AAAGATTCAG
37981 TGAACGCCAG TAATATTGGT ATGGCTGTGT ACGGGTACGT CCGACAAAGA AGAACTTATC
38041 GCGTTTGATG TTAACACCAT CTTCATAACC TGCGATAACT TTCAGGTTAC TGACATCTTC
```

```
38101   AAAATTATTC AGATAACCGA GCACCGCTTG TTGTACAGAA TCTTCGGTAA TTTTTCCCTG
38161   ATTAAGGGCA CTTTCCAGTT GGAAGAAGAA TTCTGTTTTA TTCAGGCGTA ACAGGGGTTC
38221   CAGATAGCTT TCCGGATAAG TCCGTAATAA GCGATCCC
```

N=unspecified base

PESTICIDAL AGENTS

The present invention relates to materials, agents and compositions having pesticidal activity which derive from bacteria, and more particularly from *Xenorhabdus* species. The invention further relates to organisms and methods employing such compounds and compositions.

There is an ongoing requirement for materials, agents, compositions and organisms having pesticidal activity, for instance for use in crop protection or insect-mediated disease control. Novel materials are required to overcome the problem of resistence to existing pesticides. Ideally such materials are cheap to produce, stable, have a high toxicity (either when used alone or in combination) and are effective when taken orally by the pest target. Thus any invention which provided materials, agents, compositions or organisms in which any of these properties was enhanced would represent a step forward in the art.

*Xenorhabdus* spp. in nature are frequently symbiotically associated with a nematode host, and it is known that this association may be used to control pest activity. For instance, it is known that certain *Xenorhabdus* spp. alone are capable of killing an insect host when injected into the host's hemocoel.

In addition, one extracellular insecticidal toxin from *Photorhabdus luminescens* has been isolated (this species was recently removed from the genus *Xenorhabdus*, and is closely related to the species therein). This toxin is not effective when ingested, but is highly toxic when injected into certain insect larvae (see Parasites and Pathogens of Insects Vol. 2, Eds. Beckage, N. E. et al., Academic Press 1993).

Also known are certain low-molecular weight heterocyclic compounds from *P. luminescens* and *X. nematophilus* which have antibiotic properties when applied intravenously or typically (see Rhodes, S. H. et al., PCT WO 84/01775).

Unfortunately none of these prior art materials have the ideal pesticide characteristics discussed above, and in particular, they do not have toxic activity when administered orally.

The present invention provides pesticidal agents and compositions from *Xenorhabdus* species, organisms which produce such compounds and compositions, and methods which employ these agents, compositions and organisms, that alleviate some of the problems with the prior art.

According to one aspect of the present invention there is disclosed a method of killing or controlling insect pests comprising administering cells from *Xenorhabdus* species or pesticidal materials derived or obtainable therefrom, orally to the pests.

A PCT application of CSIRO published as WO 95/00647 discloses an apparently toxic protein from *Xenorhabdus nematophilus*; however no details of the protein's toxicity are given, and certainly there is no disclosure of its use as an oral insecticide.

Thus the invention provides an insecticidal composition which:

(i) is adapted for oral administration to an insect, (ii) comprises a proteinaceous pesticidal material obtainable from a *Xenorhabdus* species, or a pesticidal fragment thereof, or a pesticidal variant or derivative of either of these, having in each case toxic activity when administered orally.

The composition may in fact comprise cells of *Xenorhabdus* or alternatively supernatant taken from cultures of cells of *Xenorhabdus* species. However, the composition preferably comprises toxins isolable from *Xenorhabdus* as illustrated hereinafter. Toxic activity has been associated with material encoded by the nucleotide sequence of FIG. 2. Thus, the composition suitably comprises a pesticidal material which is encoded by all or part of the nucleotide sequence of FIG. 2. Pesticidal fragments as well as variants or derivatives of such toxins may also be employed.

The sequence of FIG. 2 is of the order of 40 kb in length. It is believed that this sequence may encode more than one protein, each of which may regulate or be insecticidal either alone or when presented together. It is a matter of routine to determine which parts are necessary or sufficient for insecticidal activity.

As used herein the term "variant" refers to toxins which have modified amino acid sequence but which share similar activity. Certain amino acids may be replaced with different amino acids without altering the nature of the activity in a significant way. The replacement may be by way of "conservative substitution" where an amino acid is replaced with an amino acid of broadly similar properties, or there may be some non-conservative substitutions. In general however, the variants will be at least 60% homologous to the native toxin, suitably at least 70% homologous and more preferably at least 90% homologous.

The term "derivative" relates to toxins which have been modified for example by chemical or biological methods.

These toxins are novel, and they and the nucleic acids which encode them form a further aspect of the invention.

A preferred *Xenorhabdus* species is the bacteria *X. nematophilus*. Particular strains of *X. nematophilus* which are useful in the context of the invention are ATTC 19061 strain, available from the National Collection of Industrial and Marine Bacteria, Aberdeen, Scotland (NCIMB). In addition, suitable strains include two novel strains of *Xenorhabdus* which were deposited at the NCIMB on 10 Jul. 1997 and were designated with repository numbers NCIMB 40886 and NCIMB 40887. These latter strains form a further aspect of the invention.

All strains have common characteristics as set out in the following Table 1.

TABLE 1

| | Strains | | |
|---|---|---|---|
| Characteristics | ATCC 19061 | NCIMB 40887 | NCIMB 40886 |
| Gram strain | negative | negative | negative |
| Shape/size | rods up to 4 μm long | rods up to 4 μm long | rods up to 4 μm long |
| Motile | Yes | Yes | Yes |
| Bioluminescent | No | No | No |
| Colour on NBTA* | blue | blue | blue |
| insecticidal on ingestion by insects | yes | yes | yes |
| Production of Antibiotics | yes | yes | yes |
| Resistant to ampicillin (50 μg/ml) | yes | yes | yes |
| colony morphology/ colour | circular convex cream | circular convex cream | circular convex cream |

*NBTA (Oxoid nutrient agar containing 0.0025% bromothymol blue and 0.004% tetrazolium chloride)

Preferably the pest target is an insect, and more preferably it is of the order Lepidoptera, particularly *Pieris brassicae, Pieris rapae*, or *Plutella xylostella* or the order Diptera, particularly *Culex quinquefaciatus*.

In a preferred embodiment of the invention, cells from *Xenorhabdus* species or agents derived therefrom are used in conjunction with *Bacillus thuringiensis* as an oral pesticide.

In further embodiments, rather than using *Bacillus thuringiensis* itself, pesticidal materials obtainable from *B. thuringiensis* (e.g. delta endotoxins or other isolates) are used in conjunction with *Xenorhabdus* species.

The term 'obtainable from' is intended to embrace not only materials which have been isolated directly from the bacterium in question, but also those which have been subsequently cloned into and produced by other organisms.

Thus the unexpected discovery that bacteria of the genus *Xenorhabdus*(and materials derived therefrom) have pesticidal activity when ingested, and that such bacteria and materials can be used advantageously in conjunction with *B. thuringiensis* (and toxins or materials derived therefrom), forms the basis of a further aspect of the present invention. The pesticidal activity of *B. thuringiensis* isolates alone have been well documented. However, synergistic pesticidal activity between such isolates and bacteria of the *Xenorhabdus* species (or materials derived therefrom) has not previously been demonstrated.

In still further embodiments of the invention, culture supernatant taken from cultures of *Xenorhabdus* species, particularly *X. nematophilus*, is used in place of cells from *Xenorhabdus* species in the methods above.

All of these methods can be employed, inter alia, in pest control.

The invention also makes available pesticidal compositions comprising cells from *Xenorhabdus* species, preferably *X. nematophilus*, in combination with *B. thuringiensis*. As with the methods above, a pesticidal toxin from *B. thuringiensis* (preferably a delta endotoxin) may be used as an alternative to *B. thuringiensis* in the compositions of the present invention Likewise, culture supernatant taken from cultures of *Xenorhabdus* species, preferably, *X. nematophilus* may be used in place of cells from *Xenorhabdus* species.

Such compositions can be employed, inter alia, for crop protection eg. by spraying crops, or for livestock protection. In addition, compositions of the invention may be used in vector control.

The invention further encompasses novel pesticidal agents which can be isolated from *Xenorhabdus* spp. Techniques for isolating such agents would be understood by the skilled person.

In particular, such techniques include the separation and identification of toxin proteins either at the protein level or at the DNA level.

The applicants have cloned and partially sequenced a region of DNA from *Xenorhabdus* NCIMB 40887 which region codes for insecticidal activity and this is shown as FIG. 2 (SEQ ID NO. 1) hereinafter. Thus in a preferred embodiment the invention also provides a toxin which is encoded by DNA of SEQ ID No. 1 or a variant or fragment thereof.

The invention also provides a recombinant DNA which encodes such a toxin. The recombinant DNA of the invention may comprise the sequence of FIG. 2 or a variant or fragment thereof. Other DNA sequences may encode similar proteins as a result of the degeneracy of the genetic code. All such sequences are encompassed by the invention.

The sequence provided herein is sufficient to allow probes to be produced which can be used to identify and subsequently to extract DNA of toxin genes. This DNA may then be cloned into vectors and host cells as is understood in the art.

DNA which comprises or hybridises with the sequence of FIG. 2 under stringent conditions forms a further aspect of the invention.

The expression "hybridises with" means that the nucleotide sequence will anneal to all or part of the sequence of FIG. 2 under stringent hybridisation conditions, for example those illustrated in "Molecular Cloning", A Laboratory Manual" by Sambrook, Fritsch and Maniatis, Cold Spring Habor Laboratory Press, Cold Spring Harbor, N.Y.

The length of the sequence used in any particular analytical technique will depend upon the nature of the technique, the degree of complementarity of the sequence, the nature of the sequence and particularly the GC content of the probe or primer and the particular hybridisation conditions employed. Under high stringency, only sequences which are completely complementary will bind but under low stringency conditions, sequences which are 60% homologous to the target sequence, more suitably 80% homologous, will bind. Both high and low stringency conditions are encompassed by the term "stringent conditions" used herein.

Suitable fragments of the DNA of FIG. 2, i.e. those which encode pesticidal agents may be identified using standard techniques. For example, transposon mutagenesis techniques may be used, for example as described by H. S. Siefert et al., Proc. Natl. Acad. Sci. USA, (1986) 83, 735–739. Vectors such as the cosmid cHRIMI, can be mutated using a variety of transposons and then screened for loss of insectidal activity. In this way regions of DNA encoding proteins responsible for toxic activity can be identified.

For example, the mini-transposon mTn3(HIS3) can be introduced into a toxic *Xenorhabdus* clone such as cHRIM1, hereinafter referred to as clone 1, by electroporating cHRIM1 DNA into *E. coli* RDP146(pLB101) and mating this strain with *E. coli* RDP146(pOX38), followed by *E. coli* NS2114Sm. The final strain will contain cHRIM1DNA with a single insertion of the transposon mTn3(HIS3). These colonies can be cultured and tested for insecticidal activity as described in Example 8 hereinafter. Restriction mapping or DNA sequencing can be used to identify the insertion point of mTn3(HIS3) and hence the regions of DNA involved in toxicity. Similar approached can be used with other transposons such as Tn5 and mTn5.

Site directed mutagenesis of cHRIM1 as outlined in "Molecular Cloning, A Laboratory Manual" by Maniatis, Fritsch and Sambrook, (1982) Cold Spring Harbor, can also be used to test the importance of specific regions of DNA for toxic activity.

Alternatively, subcloning techniques can be used to identify regions of the cloned DNA which code for insecticidal activity. In this method, specific smaller fragments of the DNA are subcloned and the activity determined. To do this, cosmid DNA can be cut with a suitable restriction enzyme and ligated into a compatible restriction site on a plasmid vector, such as pUC19. The ligation mix can be transformed into *E. coli* and transformed clones selected using a selection marker such as antibiotic resistance, which is coded for on the plasmid vector. Details of these techniques are described for example in Maniatis et al, supra, (see p390–391) and Methods in Molecular Biology, by L. G. Davies, M. D. Dibner and J. F. Battey, Elsevier, (see p222–224).

Individual colonies containing specific cloned fragments can be cultured and tested for activity as described in Example 8 hereinafter. Subclones with insecticidal activity can be further truncated using the same methodology to further identify regions of the DNA coding for activity.

The invention also discloses an isolated pesticidal agent characterised in that the agent is obtainable from cultures of *X. nematophilus* or variants thereof, has oral pesticidal activity against *Pieris brassicae, Pieris rapae* and *Plutella xylostella*, is substantially heat stable to 55° C., is proteinaceous, acts synergistically with *B. thuringiensis* cells as an oral pesticide and is substantially resistant to proteolysis by trypsin and proteinase K.

By 'substantially heat stable to 55° C.' is meant that the agent retains some pesticidal activity when tested after heating the agent in suspension to 55° C. for 10 minutes, and preferably retains at least 50% of the untreated activity.

By 'substantially resistant to proteolysis' is meant that the agent retains some pesticidal activity when exposed to proteases at 30° C. for 2 hours and preferably retains at least 50% of the untreated activity.

By 'acts synergistically' is meant that the activity of the combination of components is greater than one might expect from the use of the components individually. For example, when used in conjunction with *B. thuringiensis* cells as an oral pesticide, the concentration of *B. thuringiensis* cellular material necessary to give 50% mortality in a *P. brassicae* when used alone is reduced by at least 80% when it is used in combination the agent at a concentration sufficient to give 25% mortality when the agent is used alone.

It has been found that the activity of the material is retained by 30 kDa cut-off filters but is only partly retained by 100 kDa filters.

Preferably the agent is still further characterised in that the pesticidal activity is lost through treatment at 25° C. with sodium dodecyl sulphate (SDS–0.1% 60 mins) and acetone (50%, 60 mins).

Clearly the characterising properties of the isolated agent described above can be utilised to purify it from, or enrich its concentration in, *Xenorhabdus* species cells and culture medium supernatants. Methods of purifying proteins from heterogenous mixtures are well known in the art (eg. ammonium sulphate precipitation, proteolysis, ultrafiltration with known molecular weight cut-off filters, ion-exchange chromatography, gel filtration, etc.). The oral pesticidal activity provides a convenient method of assaying the level of agent after each stage, or in each sample of eluent. Such methodology does not require inventive endeavour by those skilled in the art.

The invention further discloses oral pesticidal compositions comprising one or more agents as described above. Such compositions preferably further comprise other pesticidal materials from non-*Xenorhabdus* species.

These other materials may be chosen such as to have complementary properties to the agents described above, or act synergistically with it.

Preferably the oral pesticidal composition comprises one or more pesticidal agents as described above in combination with *B. thuringiensis* (or with a toxin derived therefrom, preferably endotoxin).

Recombinant DNA encoding said proteins also forms a further aspect of the invention. The DNA may be incorporated into an expression vector under the influence of suitable control elements such as promoters, enhancers, signal sequences etc. as is understood in the art. These expression vectors form a further aspect of the invention. They may be used to transform a host organism so as to ensure that the organism produces the toxin.

The invention further makes available a host organism comprising a nucleotide sequence coding for a pesticial agent as described above.

Methods of cloning the sequence for a characterised protein into a host organism are well known in the art. For instance the protein may be purified and sequenced: as activity is not required for sequencing, SDS gel electrophoresis followed by blotting of the gel may be used to purify the protein. The protein sequence can be used to generate a nucleotide probe which can itself be used to identify suitable genomic fragments from a *Xenorhabdus* gene library. These fragments can then be inserted via a suitable vector into a host organism which can express the protein. The use of such general methodology is routine and non-inventive to those skilled in the art. Such techniques may be applied to the production of *Xenorhabdus* toxins other than those encoded by the sequence of FIG. 2.

It may be desirable to manipulate (eg. mutate) the agent by altering its gene sequence (and hence protein structure) such as to optimise its physical or toxicological properties.

It may also be desirable for the host to be engineered or selected such that it also expresses other proteinaceous pesticidal materials (eg. delta-endotoxin from *B. thuringiensis*). Equally it may be desirable to generate host organisms which express fusion proteins composed of the active portion of the agent plus these other toxicity enhancing materials.

A host may be selected for the purposes of generating large quantities of pesticidal materials for purification e.g. by using *B. thuringiensis* transformed with the agent-coding gene. Preferably however the host is a plant, which would thereby gain improved pest-resistance. Suitable plant vectors, eg. the Ti plasmid from *Agrobacterium tumefaciens*, are well known in the art. Alternatively the host may be selected such as to be directly pathogenic to pests, eg. an insect baculovirus.

The teaching and scope of the present invention embraces all of these host organisms plus the agents, mutated agents or agent-fusion materials which they express.

Thus the invention makes available methods, compositions, agents and organisms having industrially applicable pesticidal activity, being particularly suited to improved crop protection or insect-mediated disease control.

The methods, compositions and agents of the present invention will now be described, by way of illustration only, through reference to the following non-limiting examples and figures. Other embodiments falling within the scope of the invention will occur to those skilled in the art in the light of these.

FIGURE

EXAMPLES

Example 1

Figure 1:
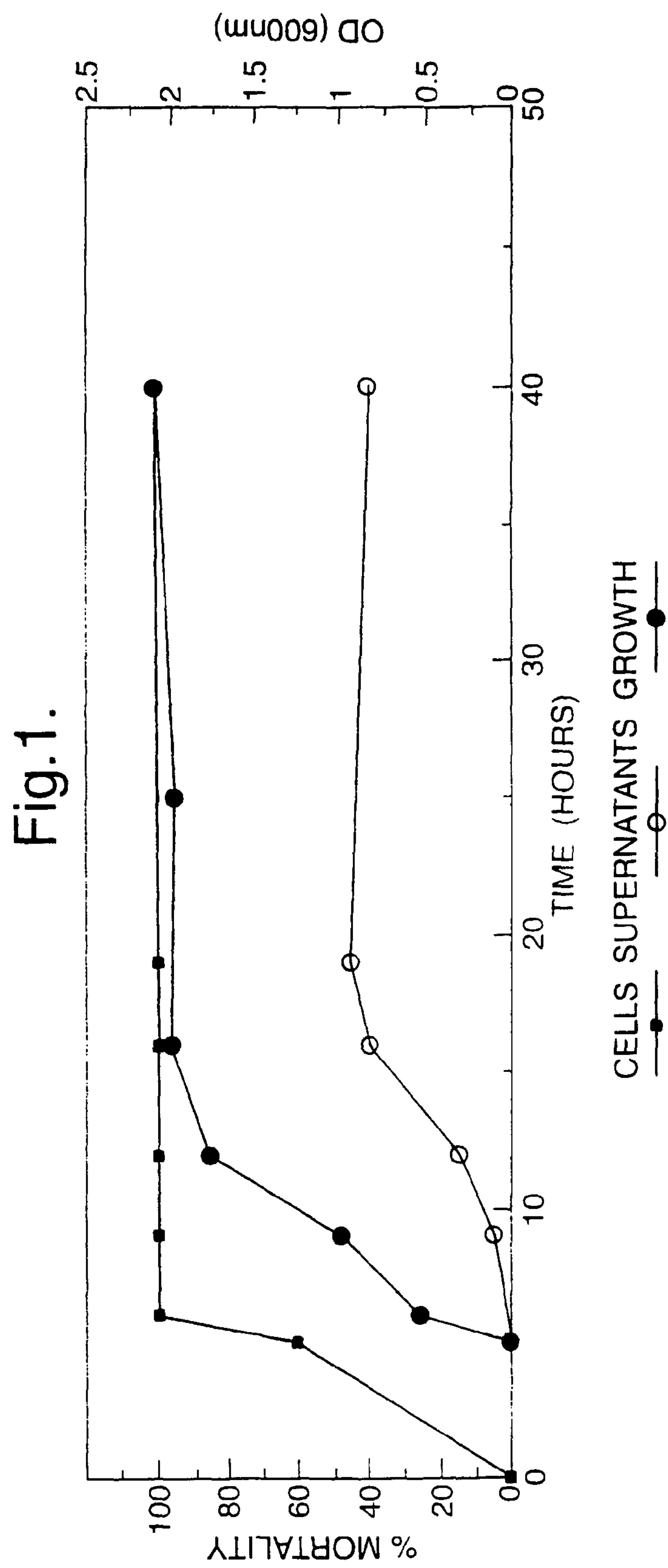
FIG. 1 shows the variation with time of the growth of *X. nematophilus* ATCC 19061 and activity of cells and supernatants against *P. brassicae* as described in Example 3.

Use of *X. nematophilus* Cells as an Oral Insecticide

CELL GROWTH: A subculture of *X. nematophilus* (ATCC 19061, Strain 9965 available from the National Collections of Industrial and Marine Bacteria, Aberdeen, Scotland) was used to inoculate 250 ml Erlenmeyer flasks each containing 50 ml of Luria Broth containing 10 g tryptone, 5 g yeast extract and 5 g NaCl per liter. Cultures were grown in the flasks at 27° C. for 40 hrs on a rotary shaker.

PRODUCTION OF CELL SUSPENSION: Cultures were centrifuged at 5000×g for 10 mins. The supernatants were discarded and the cell pellets washed once and resuspended in an equal volume of phosphate buffered saline (8 g NaCl, 1.44 g $Na_2HPO_4$ and 0.24 g of $KH_2PO_4$ per liter) at pH 7.4.

ACTIVITY OF CELL SUSPENSION TO INSECTS: The bioassays were as follows: *P. brassicae*: The larvae were allowed to feed on an artificial agar-based diet (as described by David and Gardiner (1965) London Nature, 207, 882–883) into which a series of dilutions of cell suspension had been incorporated. The bioassays were performed using a series of 5 doses with a minimum of 25 larvae per dose. Untreated and heat treated (55° C. for 10 minutes) cells were tested. Mortality was recorded after 2 and 4 days with the temperature maintained at 25° C.

| | LC50 cells/g diet | |
|---|---|---|
| Treatment | 2 days | 4 days |
| Untreated | $5.9 \times 10^5$ | $9.8 \times 10^4$ |
| Treated 55° C. | $7.1 \times 10^5$ | $1.4 \times 10^5$ |

*Aedes aegypti*: The larva were exposed to a series of 5 different dilutions of cell suspension in deionised water. The biosassays were performed using 2 doses per dilution of 50 ml cell suspension in 9.5 cm plastic cups with 25 second instar larvae per dose. Untreated and heat-treated (55° C. or 80° C. for 10 minutes) cells were tested. Mortality was recorded after 2 days with the temperature maintained at 25° C.

| Treatment | LC50 cells/ml 2 days |
|---|---|
| Untreated | $5.1 \times 10^6$ |
| Treated 55° C. | $7.4 \times 10^6$ |
| Treated 80° C. | $>10^8$ |

*Culex guinguefaciatus*: The larvae were exposed to a single concentration cell suspension containing $4\times10^7$ cells/ml. The biosassays were performed using 2 50 ml cell suspensions in 9.5 cm plastic cups with 25 second instar larvae per cup. Untreated and heat-treated (55° C. or 80° C. for 10 minutes) cells were tested. Mortality was recorded after 2 days with the temperature maintained at 25° C.

| Treatment | % Mortality 2 days |
|---|---|
| Untreated | 100 |
| Treated 55° C. | 100 |
| Treated 80° C. | 0 |

Thus these results clearly show that cells from *X. nematophilus* are effective as an oral insecticide against a number of insect species (and are particularly potent against *P. brassicae*). The insecticidal activity is not dependent on cell viability (i.e is largely unaffected by heating to 55° C. which reduces cell viability by >99.99%) but is much reduced by heating to 80° C., which denatures most proteins.

Example 2

Use of *X. nematophilus* Supernatant as an Oral Insecticide

CELL GROWTH: Cultures were grown as in Example 1.

PRODUCTION OF SUPERNATANT: Cultures were centrifuged twice at 10000 g for 10 mins. The cell pellets were discarded.

ACTIVITY OF SUPERNATANT TO INSECTS: The Bioassay was as follows:

Activity against neonate *P. brassicae* and two day old *Pieris rapae* and *Plutella xylostella* larvae was measured as for *P. brassicae* in Example 1, but using a series of untreated dilutions of supernatant in place of of cell supensions and with mortality being recorded after 4 days only.

| Insect species | LC50 (μl supernatant/g diet) 4 days |
|---|---|
| *P. brassicae* | 22 |
| *P. rapae* | 79 |
| *P. xylostella* | 135 |

In addition, size-reducing activity (62% reduction in 7 days) against *Mamestra brassicae* was detected in larvae fed on an artificial diet containing *X. nematophilus* supernatant (results not shown).

Thus these results clearly show that the supernatant from *X. nematophilus* culture medium is effective as an oral insecticide against a number of insect species, and are particularly potent against *P. brassicae.*

The heating of supernatants to 55° C. for 10 minutes caused a partial loss of activity while 80° C. caused complete loss of activity. Activity was also completely lost by treatment with SDS (0.1% w/v for 60 mins) and Acetone (50% v/v for 60 mins) but was unaffected by Triton X-100 (0.1% 60 mins), non-diet P40 (0.1% 60 mins), NaCl (1 M for 60 mins) or cold storage at 4° C. or −20° C. for 2 weeks. All of these properties are consistent with a proteinaceous agent.

The general mode of action of *X. nematophilus* cells and supernatants i.e. reduction in larval size and death within 2 days at high dosages, and other properties, eg. temperature resistence, appear to be similar suggesting a single agent or type of agent may be responsible for the oral insecticide activity activities of both cells and supernatants.

Example 3

Timescale for Appearance of Ingestable Insecticidal Activity

CELL GROWTH: 1 ml of an overnight culture of *X. nematophilus* was used to inoculate an Erlenmeyer flask. Cells were then cultured as in Example 1. Growth was estimated by measuring the optical density at 600 nm.

PRODUCTION OF CELL SUSPENSION AND SUPERNATANTS: These were produced as in Examples 1 and 2.

ACTIVITY OF CELLS AND SUPERNATANTS AGAINST *P. BRASSICAE*: The cell suspension bioassay was carried out as in Example 1, but using a single dose of suspended cells equivalent to 50 μl of broth/g diet and measuring mortality after 2 days. The cell supernatant bioassay was carried out as in Example 2, but using a single dose equivalent to 50 μl supernatant/g diet (i.e. more than twice the LC50) and measuring mortality after 2 days.

The results are shown in FIG. 1. Thus these results clearly show that cells taken from *X. nematophilus* culture medium are highly effective as an oral insecticide against *P. brassicae* after only 5 hours, and supernatants are highly effective after 20 hours. Although some slight cell lysis was observed in the early stages of growth, no significant cell lysis was observed after this point demonstrating that the supernatant activity may be due to an authentic extracellular agent (as opposed to one released only after cell breakdown).

Example 4

Synergy Between *X. nematophilus* Cells and *B. thuringiensis* Powder Preparations CELL GROWTH AND SUSPENSION: *X. nematophilus* cells were grown and suspended as in Example 1. *B. thuringiensis* strain HD1 (from *Bacillus* Genetic Stock Centre, The Ohio State University, Columbus, Ohio 43210, USA) was cultured, harvested and formulated into a powder as described by Dulmage et al.(1970) J. Invertebrate Pathology 15, 15–20.

ACTIVITY OF *X. NEMATOPHILUS* CELLS AND *B. THURINGIENSIS* POWDER AGAINST *P. BRASSICAE*: The bioassays was carried out using *X. nematophilus* and *B. thuringiensis* in combination or using *B. thuringiensis* cell powder alone. Bioassays were carried out as in Example 1 but with various dilutions of *B. thuringiensis* powder in place of *X. nematophilus*. For the combination experiment, a constant dose of *X. nematophilus* cell suspension sufficient to give 25% mortaility was also added to the diet. Mortality was recorded after 2 days.

| Bioassay | LC50 (μg Bt powder/g diet) 2 days |
|---|---|
| B.t. alone | 1.7 |
| B.t. plus *X. nematophilus* | 0.09 |

These results clearly demonstrate the synergism between *X. nematophilus* cells and *B. thuringiensis* powder when acting as an oral insecticide against *P. brassicae*.

Example 5

Synergy Between of *X. nematophilus* Supernatants and *B. thuringiensis* Powder

CELL GROWTH AND PRODUCTION OF SUPERNATANTS: *X. nematophilus* cells were grown and supernatants prepared as in Example 2. *B. thuringiensis* was grown and treated as in Example 4.

ACTIVITY OF *X. NEMATOPHILUS* SUPERNATANTS AND Bt CELL POWDER AGAINST *P. BRASSICAE:*

The bioassays were carried out using *X. nematophilus* supernatants and *B. thuringiensis* in combination or using *B. thuringiensis* powder alone. The Bioassay against neonate *P. brassicae* and two day old *Pieris rapae* and *Plutella xylostella* larvae were measured as in Example 2 but with various dilutions of *B. thuringiensis* in place of *X. nematophilus*. For the combination experiment, a constant dose of *X. nematophilus* supernatant sufficient to give 25% mortality was also added to the diet. Mortality was recorded after 4 days.

| Insect species | $LC_{50}$ (μg Bt powder/g) diet | |
|---|---|---|
| | Bt alone | Bt plus Xn |
| *P. brassicae* | 1.4 | 0.12 |
| *P. rapae* | 2.5 | 0.26 |
| *P. xylostella* | 7.2 | 0.63 |

These results clearly demonstrate the synergism between *X. nematophilus* supernatants and *B. thuringiensis* powder when acting as an oral insecticide against several insect species. The fact that both *X. nematophilus* cells and supernatants demonstrate this synergism strongly suggests that a single agent or type of agent is responsible for the demonstrated activities.

Example 5

Characterisation of Insecticidal Agent from *X. nematophilus* Supernatant by Proteolysis CELL GROWTH AND PRODUCTION OF SUPERNATANTS: *X. nematophilus* cells were grown and supernatants prepared as in Example 2.

PROTEOLYSIS OF SUPERNATANT: Culture supernatant (50 ml) was dialysed against 0.5 M NaCl (3×1 l) for 48 hours at 4° C. The volume of the supernatant in the dialysis tube was reduced five-fold by covering with polyethylene glycol 8000 (Sigma chemicals). Samples were removed and treated with either trypsin (Sigma T8253=10,000 units/mg) or proteinase K (Sigma P0390=10 units/mg) at a concentration of 0.1 mg protease/ml sample for 2 hours at 30° C.

ACTIVITY OF PROTEASE TREATED SUPERNATANT AGAINST *P. BRASSICAE*: The boassay against neonate *P. brassicae* larvae was carried out by spreading 25 μl of each 'treatment' on the artificial agar-based diet referred to in Example 1 in a 4.5 cm diameter plastic pot. Four pots each containing 10 larvae were used for each treatment. Mortalities were recorded after 1 and 2 days. Controls using water only, trypsin (0.1 mg/ml) and proteinase K (0.1 mg/ml) were also tested in the same way.

| Treatment | % Mortality | |
|---|---|---|
| | 1 day | 2 days |
| Untreated supernatant | 60 | 100 |
| Proteinase K treated supernatant | 45 | 100 |
| Trypsin treated supernatant | 40 | 100 |
| All controls (no supernatant) | 0 | 0 |

Example 6

Entomocidal Activity of Other *Xenorhabdus*

Using the methodology of Examples 1 and 2, four different *xenorhabdus* strains were tested against insect pests.

The results obtained were as follows:

| I) Activity to *Pieris brassicae* | | |
|---|---|---|
| Strain deposit no/code | Cells $10^6$/grm diet % mortality | Supernatant LC50 µl/gram of diet |
| NCIMB 40887 | 100 | 0.09 |
| 0014 | 100 | 0.52 |
| 0015 | 80 | 3.73 |
| NCIMB 40886 | 100 | 0.05 |

It was found that entomocidal activity of cells and supernatant was reduced by more than 99% when all four strains were heated at 80° C. for 10 minutes.

| II) Activity to mosquitoes (*Aedes aegypti*) Bacteria added at the rate of $10^7$ cells/ml of water | |
|---|---|
| Strain deposit no/code | Cells $10^6$/grm diet % mortality |
| NCIMB 40887 | 0 |
| 0014 | 40 |
| 0015 | 45 |
| NCIMB 40886 | 95 |

Furthermore, all strains significantly reduced the growth of *Heliothis virescens.*

Example 7

Cloning of Toxin Genes from Strains of *Xenorhabdus*

Total cellular DNA was isolated from NCIMB 40887 and ATCC 19061 using a Quiagen genomic purification DNA kit. Cells were grown in L borth (10 g tryptone, 5 g yeast extract and 5 g NaCl per l) at 28° C. with shaking (150 rpm) to an optical density of 1.5 $A_{600}$. Cultures were harvested by centrifugation at 4000×g and resuspended in 3.5 mls of buffer B1 (50 mM Tris/HCl, 0.05% Tween 20, 0.5% Triton X-100, pH7.0) and incubated for 30 mins at 50° C. DNA was isolated from bacterial lysates using Quiagen 100/G tips as per manufacturers instructions. The resulting purified DNA was stored at −20° C. in TE buffer (10 mM Tris, 1 mM EDTA, pH 8.0).

A representative DNA library was produced using total DNA of NCIMB 40887 and ATTC 19061 partially digested with the restriction enzyme Sau3a. Approximately 20 µg of DNA from each strain was incubated at 37° C. with 0.25 units of the enzyme. At time intervals of 10, 20, 30, 45 and 60 minutes, samples were withdrawn and heated at 65° C. for 15 minutes. To visualise the size of the DNA fragments, the samples were electrophoresed on 0.5% w/v agarose gels.

The DNA samples which contained the highest proportion of 30 to 50 kb fragments were combined and treated with 4 units of shrimp alkaline phosphatase (Boehringer) for 15 minutes at 37° C., followed by heat treatment at 65° C. to inactivate the phosphatase.

The size selected DNA fragments were ligated into the BamH1 site of the cosmid vector SuperCos! (Stratagent) and packaged into the *Escherichia coli* strain XL Blue 1, using a Gigapack II packaging kit (Stratgene) in accordance with the manufacturers instructions.

To select for cosmid clones with entomocidal activity, individual colonies selected on L agar plates containing 25 µg/ml ampicillin, were grown in L broth (containing 25 µg/ml ampicillin) overnight at 28° C. Broth cultures (50 µl) were individually spread onto the surface of insect diet contained in 4.5 cm diameter pots, as described in Example 5. To each container 10 neonate *P. brassicae* larvae were added. Larvae were examined after 24, 72 and 96 hours recording mortality and size of surviving larvae. A total of 220 clones of NCIMB 40887 were tested, of which two were found to cause reduction in larval growth and death within 72 hours. Of 370 clones from ATTC 19061, one was found to cause larval death within 72 hours.

Example 8

Activity of Cloned Toxin Genes to *Pieris brassicae*

The three active clones from Example 7 were grown in L broth, containing 25 µg/ml ampicillin, for 24 hours at 28° C., on a rotary shaker at 150 rpm. The activity of the toxin clones to neonate larvae were performed by incorporation of whole broth cultures into insect diet, as described in Example 1.

| Clone No | Strain | LC50 (µl broth/g insect diet) |
|---|---|---|
| 1 | NCIMB 40887 | 13.03 |
| 2 | NCIMB 40887 | 16.7 |
| 3 | ATTC 19061 | 108.7 |
| Control* | | No effect at 100 µl/g |

*XL1 Blue *E. coli* broth

When *E. coli* toxin clones were heated at 80° C. for 10 minutes and added to the diet at a rate of 100 µl/g, no activity to larvae was detected. Highlighting the heat sensitivity of the toxins.

Example 9

Sequencing of the Cloned Toxin from NCIMB 40887

Figures 2, 3:
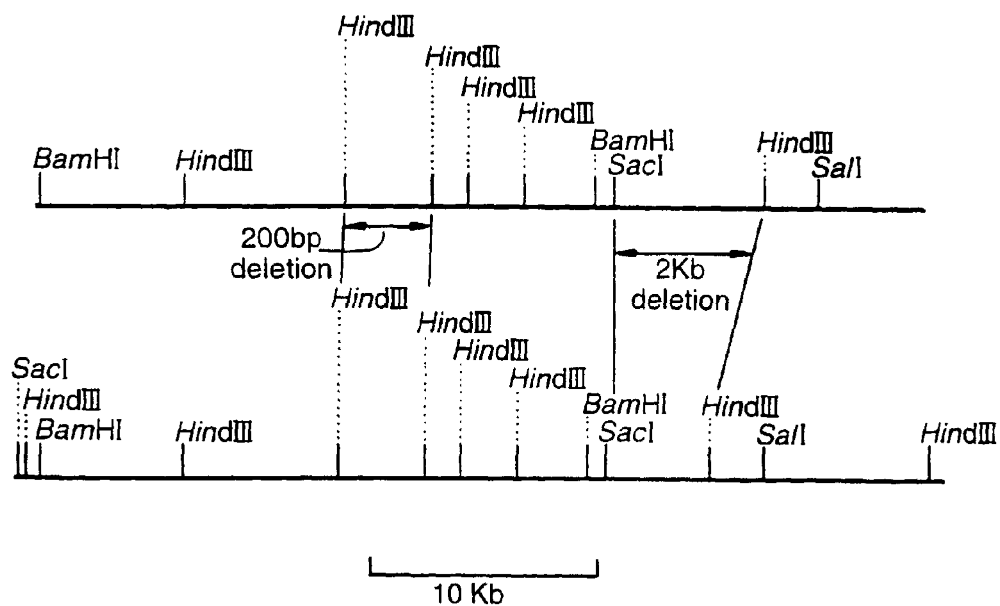
FIG. 2 shows the sequence of a major part of a cloned toxin gene from *Xenorhabdus.*
FIG. 3 shows a comparison of the restriction maps of cloned toxin genes from two strains of *Xenorhabdus* (clone 1 above and clone 3 below).

Cosmid DNA of the entomocidal clone 1 above from NCIMB 40887 was purified using the Wizard Plus SV DNA system (Promega) in accordance with the manufacturers instructions. A partial map of the cloned fragment was obtained using a range of restriction enzymes EcoRI, BamH1, HindIII, Sal1 and Sac1 as shown in FIG. 3. DNA sequencing was intiatiated from pUC18 and pUC19 based sub-clones of the cosmid, using the enzymes EcoR1, BamH1, HindIII, EcoRV and PvuII. Sequence gaps were filled using a primer walking approach on purified cosmid DNA. Sequence reactions were performed using the ABI PRISM™ Dye Terminator Cycle Sequencing Ready Reaction Kit with AmmpliTaq DNA polymerase FS according to the manufacturers instructions. The samples were analysed on an ABI automated sequencer according to the manufacturers instructions. The major part of the DNA sequence for the cloned toxin fragment is shown in FIG. 2.

Example 10

Restriction Map of Cloned Toxin from Clone 3

Cosmid DNA of the entomocidal clone 3 above was purified as described in Example 9. A restriction map of the cloned fragment was obtained using the restriction enzymes BamH1, HindIII, Sal1 and Sac1 and this is shown in FIG. 3. When compared with the map from clone 1 (FIG. 3) it is clear that over the regions which overlap, the restriction maps are very similar. The only detectable difference between the two clones was a reduction in size of two HindIII fragments in clone 3, corresponding to the 11.4 kb and 7.2 kb HindIII fragments in clone 1 by approximately 2 Kb and 200 bp respectively. These results indicate the overall relatedness of the DNA region coding for toxicity in the two bacterial strains.

Example 11

Southern Blot Hybridisation Experiments

A 10.3 kb BamH1-Sal1 fragment of the DNA from clone 1 was used as a probe to hybidise to total HindIII digested DNA of the *Xenorhabdus* strains ATCC 19061, NCIMB 40886 and NCIMB 40887. Hybridisation was performed with 20 ng/ml of DIG labelled DNA probe at 65° C. for 18 hours. Filters were washed prior to immunological detection twice for 5 minutes with 2×SSC (0.3M NaCl, 30 mM sodium citrate, pH 7.0)/0.1% (w/v) sodium dodecyl sulphate at room temperature, and twice for 15 minutes with 0.1×SSC (15 mM NaClm 1.5 mM sodium citrate, pH 7.0) plus 0.1% sodium dodecyl sulphate at 65° C. The probe was labelled and experiments performed in accordance with manufacturers instructions, using a non-radioactive DIG DNA labelling and detection kit (Boehringer). The probe hybridised to a HindIII fragment of approximately 8 kb in all three strains as well as an 11.4 kb fragment in NCIMB 40887 and an approximate 9 kb fragment in both NCIMB 40886 and ATCC 19061. These results show that strains NCIMB 40886 and ATCC 19061 contain DNA with close homology to the toxin gene of clone 1 above, confirming the similarity between the toxins produced by the three strains.

The invention claimed is:

1. A composition comprising at least one of (i) cells, into which a nucleotide sequence of FIG. 2 (SEQ ID No 1) has been introduced and (ii) a cellular extract from said cells, said cells and cellular extract having toxic activity when administered orally to an insect.

2. A composition according to claim 1 which comprises a further pesticidal material not obtainable from *Xenorhabdus*.

3. A composition according to claim 2 wherein the said further pesticidal material comprises a material obtainable from *B. thuringiensis*.

4. A composition according to claim 3 which further comprises cells of *B. thuringiensis*.

5. A composition according to claim 4 wherein the pesticidal material obtainable from *B. thuringiensis* comprises the delta endotoxin.

6. A composition according to claim 1 which further comprises an agriculturally acceptable carrier.

7. A composition according to claim 6, wherein the carrier comprises items of insect diet.

8. A method for killing or controlling insect pests, which method comprises administering to a pest or the environment thereof a composition according to claim 1.

9. A method according to claim 8, wherein the pests are insects from the order Lepidoptera or Diptera.

10. A method for killing or controlling insect pests, which method comprises administering orally to the insect a composition according to claim 1.

11. A composition according to claim 1 wherein said nucleotide sequence is the nucleotide sequence of FIG. 2 (SEQ ID No. 1).

12. A composition according to claim 1 wherein said nucleotide sequence is a fragment of FIG. 2 (SEQ ID No. 1) encoding a protein having said toxic activity.

* * * * *

SEQUENCE LISTING

```
<160> NUMBER OF SEQ ID NOS:  1

<210> SEQ ID NO 1
<211> LENGTH: 38258
<212> TYPE: DNA
<213> ORGANISM: Xenorhabdus
<220> FEATURE:
<221> NAME/KEY: misc_feature
<222> LOCATION: 35490, 35492, (35499)...(35519)
<223> OTHER INFORMATION: n at any position = a or c or g or t

<400> SEQUENCE: 1

tccacaattg ccggagaaaa tcagtcggga actgccggtg attattcgtc acttattaaa     60

cgaatttgcc gaccagaata aggctaaaaa actgctacag gcgcaacgcg actcgaacga    120

agcgttaacg gtaaagagtc attcggatcc gctgtatcgc ttttgtggtt atctggtgtc    180

tgtcaatgat atgaccggaa tgaagatggg caataaaaac attagcccac gagcaccgag    240

attgtacttg tatcatgcct atctctcttt tatggaagcg cacggctttg aacgtccgtt    300

aacactgact aagtttggtg aatccatccc caagattatg ctggaatacc ggaaggagta    360

tcgaaaagtg cgaaccaaga aaggctattc ctataacgtg gaattatcgg aagaggccga    420

agaatggcta ccgtcagtgc ctgagtgtcg agactttaaa tcacctgtat aaaactttga    480

gctttaagtc tgcactccat acacaactta aaatatctaa ttgtatttaa aagaaaataa    540

tagatgtata gttatttttt aactatacat aagctctaca tgctcttcat tcgtgtaaaa    600

aatgggtgaa caggtgatac agtcagtgaa tatcatatta attaccgtaa acccagatgt    660

agcaaggctt tcagggaatt gtgcagaggg tgcataactg agagggtgaa aaagattttc    720

agggggcctt atggcaggta aacaaaatca gaagcaaata ccgtgcacaa tctggttttt    780

attttttggt actacctcaa attaaaatga tgtaatcatc tgattttatt taagaataga    840

agttaatcac aatttcattg atggactttc attcacactg gtatagataa ataattctgt    900

tatatcctgt ttcattacgc attcatcagg agtgctgtta caggagacaa gaatgtcaca    960

catcatttac ttgtcgttaa agggcaagaa gcagggttta atttcagcgg gttgttcaac   1020

gcctgaatca attggaaatc gctatcaaaa aggacgtgaa gatcaaatac aggtattgag   1080

cctgaatcat tcgatgagcc gtgaccagaa tgttaatcat caacccgtca gttttgtgaa   1140
```

-continued

```
acccattgat aaatcctctc ccctgtttgc tggatgccag ttttgtgcat tacaggacaa   1200
gccagatggg acaactggag ttcttttatg aaatcaagct gaccagtgcc acgattgtgg   1260
atatttccta taattatccg gcattcaatc aatgataatg gtgcgatacc ccatgaagtg   1320
gtgatgctcg attataagtc catttcatgc aaccacatcg ccgcaggact tcgggctaca   1380
gcatacgcaa ttagccggaa gtgaagaagc aagccgcttt tatctggggt ctcgaatgtt   1440
aagccactta agaagccgct ggttgaagaa accccggtaa aacccgctaa acatcatgcc   1500
cgttatcgtt gtgtggatga tgacggcaat cttttaaccg aacgcaagta tcgggtttgc   1560
ctgccggatg gtcagataaa agaaggaaag actgataaac aaggttacac ccaatggcat   1620
cttacggatg acaaaaataa acttgaattt catattttaa aggattaata ccatgccagc   1680
ctataccgtt cagacaaaaa tagaatccaa cgtacctgtt gaaaacctgc tttacgactt   1740
aaccatttat cgtaaggatg caaaaggaaa tttccatatc ttgcttgatg tttttcagga   1800
gaaactacag agtaattatg aaacacaaca gcatatcacg caggaaatag acgacgatct   1860
ttctgtgatt tatattatgc aaattatgct tcaccgcaaa catggctcaa atatatttcc   1920
ggcactgcaa acccatttta agaaaatgta taccctcggt gaattaactt ccggtaaagc   1980
ctgttcggag aaaaaacggg aaaatgcctg ttattttgaa agtacagttg aaacaaaacc   2040
tgtcagcgac ggggataata ccgttgactt aaatatcact attcctgaac gaccttttat   2100
tgccaaagaa tatcccattg gtcacccaca cgatccattt gaaaaaagta aaattgaatc   2160
ataaatacag gacaggttat cgaaaagaat ttatccggat caaaatggag caagtttatg   2220
tcagggcgcg agcacactat tttagctgcg tttttaagat gattatctct taatgttcag   2280
ttttaatagt gtttttatcg agtgaaattt aatcgcacag gcaattcttt agacttttat   2340
agaaaactaa agaattaaag aacaagattg acattttaag ttcaaatatt aatcaaagta   2400
tgctcgcgcc ctgagtttat gtggccctgc cgcttttttt tattgcctgc caatagatag   2460
accagatatt tatgagcaag cggcacgaga attatggcaa tatggccgaa ctaaaattgg   2520
tcaactggaa attaagccgg gtgagggttg ccgacatcct aaaggtactt tttataatca   2580
atatggtgaa agaatatctg ggttagattg gctgacattg gcaagcctaa gagattcaga   2640
aaatatgatg atgaggttga tgatgaagta gctggtatta caatgtgggg aaaattgaca   2700
gaatggtttg aaaaatcagg gtatgaaaaa gtatttagta atgtcggctt atcccattct   2760
aatataaatg acatagtaac tcttagtgat tactataaca aaggatatca tgttgttact   2820
ttgatttcag caggaatgtt atcagatttt ggtgacatag aaacatcagg aaaaaatcat   2880
tggatagttt gggaaggagt agtagaaaac tatgagaaag aaaatatcac aaataattca   2940
gatctgaatc aatatgtaaa tttaaatctg ttttcatggg gtaaagtgga acatcaaatt   3000
aaaaaaaaca aatcactaga ttatgtactc aaccatattt tttgagggtt ggtttttaaa   3060
ccaatgaaat aacatgaaaa aaatattaat tatttttatt tttttacttt atggttgtgg   3120
taatccaacg ccaaaagttt taccaaaatc agagtttctt cctgatgcag tgataaatga   3180
accatatcag gcatcaatta ccatcacagg aggtgcattg aatgaaaaaa gcgtttgggt   3240
aaaaattcat cctactggct caggactaac atggaatcca aaagatagtt ctttcctata   3300
gggtggaaaa aaagaaataa gaaaagatta tcatcatata aatataacag gtaccccaaa   3360
gaagacagaa ttgataaaaa ttgaagtggt aggatttaca ttgggtacaa tgtacgcacg   3420
gaaagagttc actataaatt atactataaa agtaagggaa taattgtcac tatcagaatg   3480
gtgatttaat tcgccatttt tatactttttg tatactctct caacataatc aggattcttt   3540
```

-continued

```
cttattattt ttcatggtgc taaaaacgtt tattgcaaaa ataaattaag ttaatcagat   3600
aaattatctg cattactgtt ataatcgata acacgataac ctgactttct gcctgttctt   3660
atgaactcga agataatcct ttctgagcct gaacgaatca cattgcaacc actcgctttg   3720
aatcacccac accgggacat tcgtacgcga ggaacgggtt tactcatgct tgccagaggg   3780
agcaagccgt cccagatcac cgctgaaatc ggatgcagtc tccgggttat ctgtaattgg   3840
gttcacatgt ggcacagata gcgggattat tcggcggtca tgccggaggc cggtatctcg   3900
ccatgacgcc tgacatgatt gccactgcgc tcgaagccgc cagcgcagag tccctgacgt   3960
gcgtcgaagc caggcagggt ttccctgcct tgtacgcttg aaacgctggc gaataccctg   4020
aaaaaacagg ggctcccta taaacgcccc cgcctgtcgc ttaaaaaaag cgcaataaaa   4080
cggagtttgc tgaaaaatcc gccttgctga ataaaattaa ggccggagca cagtcaggac   4140
attaccgtct ggtctatttt gagttctggg ggcgttaaat tacacggata acacgctgtt   4200
ttaccagaca acgtcaggca gtatcacgcg agatgacgtg attgattttt tagagccggt   4260
ggccagacaa gggacaaccg cctgacattt ttagtgttgg ataatgcgcg tatccatcac   4320
gggatagagg aaaaaatcag aaatggcggg tgacgagaac acaacctgtt tttattctat   4380
cttcccgctt acagcccaga gctgtatctg attgaaatcg tctggaaaca ggccaaatac   4440
gactggcgac gttttatcac ctggactcag gatacaatgg aatatgaggt aaatacttta   4500
ttgaaaggtt atggcgacca atttgcaatt aacttttctt gagtacttag taagaataga   4560
gtcagtcgag gttttttcat ttcgggtcgt ggggatgata ctgaaaattt gtttgtaatc   4620
tctgaaaatt gctgtttctg tggctacgtc tgtcttttgg gatattgttt ccatcaagtc   4680
tgtcaacata ctgttaagtt agatgttgat aaaagagact gaattataat acaaaacaat   4740
aaatcacttg gacaatattt tatttcacat gagacattaa ggttgatttt cccaatctgg   4800
tcagttataa ccgaataagg atcttgaaaa atcatgggat cttactttta tcaaatgaag   4860
ttaacgtaaa agttgataaa gaaaattatt taattctaag tgccgttggc ataaatattt   4920
tgtgttttgt taatgaatga ataaccaggt aagctggatt ttcatttttt aattactcgt   4980
tacaatatgc tatttattta tataaagagt ttgtgcccat ttaaccagta aacaaatttg   5040
ttcaaccgta acttagcttc atcgactttt ggcctcgcct ggtcagaatc tagggccgtt   5100
atcctattta tttatgataa ataaaattta attatcttta ataagctgaa tatgtggatt   5160
tgtgctcaat cttggattca agtatgtatt ccttttggta ccctgcttta ttttaaggca   5220
gatgaagagg atgccaacat gacacaatat cgattacgac tgtaacatta aagtcagtta   5280
taaattttat gattaaaatg aaattttagt agaaaatcgt attctattcc gccatttaca   5340
atagcatcct ctttaatatc attaatctca gataaaacaa ataattacaa tgtgaataga   5400
ataatgactt acaaaataag cactaaatct tcagatgaac tcttaactga caacactatt   5460
ttataaaata attgaggtta ttatgtatag cacggctgta ttactcaata aaatcagtcc   5520
cactcgcgac ggtcagacga tgactcttgc ggatctgcaa tatttatcct tcagtgaact   5580
gagaaaaatc tttgatgacc agctcagttg gggagaggct cgccatctct atcatgaaac   5640
tatagagcag aaaaaaaata atcgcttgct ggaagcgcgt atttttaccc gtgccaaccc   5700
acaattatcc ggtgctatcc gactcggtat tgaacgagac agcgtttcac gcagttatga   5760
tgaaatgttt ggtgcccgtt cttcttcctt tgtgaaaccg ggttcagtgg cttccatgtt   5820
ttcaccggct ggctatctca ccgaattgta tcgtgaagcg aaggacttac atttttcaag   5880
```

-continued

```
ctctgcttat catcttgata atcgccgtcc ggatctggct gatctgactc tgagccagag   5940
taatatggat acagaaattt ccaccctgac actgtctaac gaactgttgc tggagctatt   6000
acccgcaaga ccggaggtga ttcggacgca ttgatggaga gcctgtcaac ttaccgtcag   6060
gccattgata ccccttacca tcagccttac gagactatcc gtcaggtcat tatgacccat   6120
gacagtacac tgtcagcgct gtcccgtaat cctgaggtga tggggcaggc ggaaggggct   6180
tcattactgg cgattctggc caatatttct ccagaactgt ataacatttt gaccgaagag   6240
attacggaaa agaacgctga tgctttattt gcgcaaaact tcagtgaaaa tatcacgccc   6300
gaaaatttcg cgtcacaatc atggatagcc aagtattatg gtcttgaact ttctgaggtg   6360
caaaaatacc tcgggatgtt gcagaatggc tattctgaca gcacctctgc ttatgtggat   6420
aatatctcaa cgggtttagt ggtcaataat gaaagtaaac tcgaagctta caaaataaca   6480
cgtgtaaaaa cagatgatta tgataaacat gtaaattact ttgatctgat gtatgaagga   6540
aataatcaat tctttatatg tgctaatttt aagatatcga gagaatttgg ggcgactctt   6600
aggaaaaact cagggacaag tggcattgtc ggcagccttt ccggtcccct ggtagccaat   6660
actaatttca aaagcaatta cttaagtaac atatctgata atgaatacag aaatggcgta   6720
aaaatatatg cctatcgcta tacgtcttcc accagcgcca caaatcaggg cggcggaata   6780
ttcacttttg agtcttatcc cctgactata tttgcgctca aactgaataa agccattcgc   6840
ttgtgcctga ctagcgggct ttcaccgaat gaactgcaaa ctatcgtacg cagtgacaat   6900
gcacaaggca tcatcaacga ctccgttctg accaaagttt tctatactct gttctacagt   6960
caccgttatg cactgagctt tgatgatgca caggtactga acggatcggt cattaatcaa   7020
tatgcccgac gatgacagtg tcagtcattt taaccgtctc tttaataccc cgccgctgaa   7080
agggaaaatc tttgaagccg acggcaacac ggtcagcatt gatccggatg aagaacaatc   7140
tacctttgcc cgttcagccc tgatgcgtgg tctggggatc aacagtggtg aactgtatca   7200
gttaggcaaa ctggcgggtg tattggacac acaaaatatc ctcacacttt ctgtccctgt   7260
tatatcttca ctgtatcgcc tcacgttact ggcccgtgcc catcagctga cggttaatga   7320
actgtgtatg ctttatggtt tttcgccgtt caatggcaaa acaacggctt ctttgtcttc   7380
cggggagttg tcacggctgg ttatctggtt gtatcaggtg acgcagtggc tgactgaggg   7440
cggaaatcac cactgaagcg atctggttat tatgtacgcc agagttcagc gggaatattt   7500
caccggaaat cagtaatctg cttaatactc tccgaccccg tattagtgaa gacatggcac   7560
aaagtagtga ccgggagctt caggctgaaa ttctcgcgcc gtttattgct gcaacgctgc   7620
atctggcgtc accagatatg gcgcggtata tcctgttgtg gactgataac ctgcggccgg   7680
gcggcctgaa tatcgccgga tttatgatgc tggtgctgaa agagacgctg agtgatgagg   7740
aaacgaccca actggttcaa ttctgccatg taatggcaca gttatcgctt tccgtgcaga   7800
cactgcgtct cagtgaagca gagctttctg tgctggtcat ttccgatttt gtggtactgg   7860
gtgcgagaag ccaaccgccg gacaacacaa tattgatact ctgttctcac tctaccgatt   7920
ccaccagtgg attaatgggc tgggaaatcc cggctctgac acgctggata tgctgcgcca   7980
agcagacact cacgggcgac agactgggcc tccgtgatgg ggctggacat cagtatggta   8040
acgcaggcca tgggttcccg ccggcgtgaa ccaacttcag tgttggcagg atatcaaccc   8100
cgtgttgcag tggatacatg tggcatcagc actgctcact gatgccgtcg gttatccgta   8160
cgctggtgaa tatccgttac gtgactgcat taaacaaagc cgagtcgaat ctgcctgcct   8220
gggataagtg gcagacgctg gcagaaaata tggcagccgg actgagtaca caacaggctc   8280
```

```
agacgctggc ggattatacc gcagagcgcc tgagtaacgt gttgtgcaat tggtttctgg   8340
cgaatatcca gccagaaggg gtgtccctgc acagccggga tgacctgtac agctatttcc   8400
tgattgataa tcaggtctct tctgccataa aaaccacccg actggcagag gccattgccg   8460
gtattcagct ctacatcaac cgggcgctga accggataga gcctaatgcc cgtgccgatg   8520
tgtcaacccg ccagtttttt accgactgga cggtgaataa ccgttacagc acctggggcg   8580
gggtgtcgcg gctggtttat tatccggaaa attacattga cccgacccag cgtatcgggc   8640
agacccggat gatggatgaa ctgctggaag atatcagcca gagtcagctc agccgggaca   8700
cggtggaaga ggcctttaaa acttacctga ccgctttgaa accgtggcag acctgaaagt   8760
tgtcagcgct atcaccgaca acgtcaacag caacaccgga ctgacctggt ttgtcggcca   8820
aacgcgggag aacctgccgg aatattactg gcgtaacgtg catatatcac ggatgcaggc   8880
gggtgaactg gccgccgatg cctggaaaga ttggacgaag attgatacag cggtcaaccc   8940
atacaaggat gcaatacgtc cggtcatatt cagggaacgt ttgcacctta tcgtgggtag   9000
aaaaagagga agtggcgaaa aatggtactg atccggtgga aacctatgac cgttttactc   9060
tgaaactggc gtttctgcgt catgatggca gttggagtgc cccctggtct tacgatatca   9120
caacgcaggt ggaggcggtc actgacaaaa aacctgacac tgaacggctg gcgctggccg   9180
catcaggctt tcagggcgag gatactctgc tggtgtttgt gtacaaaacc ggggtgagtt   9240
acccggattt tggcgacaac aataaaaatg tggcaggcat gaccatttac ggcgatggct   9300
ccttcaaaaa gatggagaac acagcactca gcgttacagc caactgaaaa atacctttga   9360
tatcattcat actcaaggca acgacttggt aagaaaggcc agctatcgtt tcgcgcagga   9420
ttttgaagtg cctgcctcgt tgaatatggg ttctgccatc ggtgatgata gtctgacggt   9480
gatggaaaac gggaatattc cgcagataac cagtaaatac tccagcgata accttgctat   9540
tacgctacat aacgccgctt tcactgtcag atatgatggc agtggcaatg tcatcagaaa   9600
caaacaaatc agcgccatga aactgacggg gttggatgaa agtcccagta cggcaatgca   9660
tttatcatcg caaataccgt taaacattat ggcggttact ctgatctggg gggcccgatc   9720
accgttttta ttaaaacgga aaaactatat tgcatcagtt caaggccact tgatgaacgc   9780
agattacact aggcgtttga ttctaacacc agttgaaaat aattattatg ccagattgtt   9840
cgagtttcca ttttctccaa acacaatttt aaacaccgtt ttcacggttg gtagcaataa   9900
aaccagtgat tttaaaaagt gcagttatgc tgttgatggt aataattctc agggcttcca   9960
gatatttagt tcctatcaat catccggctg gctggatatt gacacaggta ttaacaatac  10020
tgatgtcaaa attacggtgg tagctggcag taaaacccac acctttacgg ccagtgacca  10080
tattgcttcc ttgccggcaa acagttttga tgctatgccg tacaccttta agccactgga  10140
aatcgatgct tcatcgttgg cctttaccaa taatattgct cctctggata tcgtttttga  10200
gaccaaagcc aaagacgggc gagtgctggg taagatcaag caaacattat cggtgaaacg  10260
ggtaaattat aatccggaag atattctgtt tctgcgtgaa actcattcgg gtgcccaata  10320
tatgcagctc ggggtgtatc gtattcgtct taataccctg ctggcttctc aactggtatc  10380
cagagcaaac acgggcattg atactatcct gacaatggaa acccagcggt taccggaacc  10440
tccgttggga gaaggcttct ttgccaactt tgttctgcct aaatatgacc ctgctgaaca  10500
tggcgatgag cggtggttta aaatccatat cgggaatgtt ggcggtaaca cgggaaggca  10560
gccttattac agcggaatgt tatccgatac gtcggaaacc agtatgacac tgtttgtccc  10620
```

-continued

```
ttatgccgaa gggtattaca tgcatgaagg tgtcagattg gggttggat accagaaaat  10680
tacctatgac aacacttggg aatctgcttt cttttatttt gatgagacaa aacagcaatt  10740
tgtattaatt aacgatgctg atcatgattc aggaatgacg caacagggga tcgtgaaaaa  10800
tatcaagaaa tacaaaggat ttttgaatgt ttctatcgca acgggctatt ccgccccgat  10860
ggatttcaat agtgccagcg ccctctatta ctgggaatgt tctattacac cccgatgatg  10920
tgcttccagc gtttgctaca ggaaaaacaa ttcgacgaag ccacacaatg gataaactac  10980
gtctataatc ccgccggcta tatcgttaac ggagaaatcg ccccctggat ctggaactgc  11040
cggccgctgg aagagacact cctggaatgc caatccgttg gatgccattg atccggatgc  11100
cgtcgcacaa tatgacccga cacactataa agttgccacc tttatgcgcc tgttggatca  11160
acttattctg cgcggcgata tggcctatcg cgaactgacc cgcgatgcgt tgaatgaagc  11220
caagatgtgg tatgtgcgtg ctttggaatt gctgggtgat gagccggagg attacggcag  11280
ccaacagtgg gccgcaccgt ctctttccgt ggcgggcaac cacactgtgc aagcgggcta  11340
tcaacaagac cttacggcgc tagacaacgg agaaggttgc actcaacccc gcaacgctaa  11400
ctcgttggtg gtttggtcct gccggaatat aacccggaat caaccgatta ctggcaaacc  11460
tgcgtttgcg cctggttaac ctgcgccata atccttccat gacgggcaac cgttatcgct  11520
ggcgaattac gcgagcctac gatccgaaag cgctgctcac cagtatggta cagccttctc  11580
agggcggtag tgcagtgctg cccggcacat tgtcgttata ccgcttcccg gtgatgctgg  11640
agcgggcccg caatctggta gcgcaattaa cccagttcgg cacctctctg ctcagtatgg  11700
cagagcatga tgatgccgat gaactcacca cgttgctact acagcagggt atggaactgg  11760
cgacacagag catccgtatt cagcaacgaa ctgtcgatga agtggatgct gatattgctg  11820
tattggcaga gagccgccgc agtgcacaaa atcgtctgga aaaataccag cagctgtatg  11880
acgaggatat caaccacgga gaacagcgtg cgatgtcact gtttgatgcg gcggcaggtc  11940
agtctctggc cgggcaggcg ctctcagtag cagaaggggt ggctgactta gttccaaacg  12000
tgttcggttt cgcttgtggc ggcagtcgtt gggggggcagc actgcgtgct tccgcctccg  12060
tgatgtcgct ttctgccaca gcttcccaat attccgcaga caaaatcagc cgttcggaag  12120
cctaccgccg ccgccgtcag gagtgggaaa ttcagcgtga taatgctgac ggtgaagtca  12180
aacaaatgga tgcccagctg gaaagcctga aaatacgcgg cgaagcagca cagatgcagg  12240
tggaatatca ggagacccag caggcccata ctcaggctca gttagagctg ttacagcgta  12300
aattcacaaa caaagcgctt tacagttgga tgcgcggcaa gctgagtgct atctattacc  12360
agttctttga cctgacccag tccttctgcc tgatggcaca ggaagcgctg cgccgcgagc  12420
tgaccgacaa cggtgttacc tttatccggg gtggggcctg gaacggtacg actgcgggtt  12480
tgatggcggg tgaaacgttg ctgctgaatc tggcagaaat ggaaaaagtc tggctggagc  12540
gtgatgagcg ggcactggaa gtgacccgta ccgtctcgtt ggcacagttc tatcaggcct  12600
tatcatcaga caactttaat ctgaccgaaa aactcacgca attcctgcgt gaagggaaag  12660
gcaacgtagg agcttccggc aatgaattaa aactcagtaa ccgccagata gaagcctcag  12720
tgcgattgtc tgatttgaaa attttcagcg ataccccgga aagctttggc aatacccgtc  12780
agttgaaaca agtgagtgtc accttgccgg cgctggttgg tccgtatgaa gatatccggg  12840
cggtgctgaa ttacggcggc agcatcgtca tgccacgcgg ttgcagtgct attgctctct  12900
cccacggcgt gaatgacagt ggtcaattta tgctggattt caacgattcc cgttatctgc  12960
cgtttgaagg tatttccgtg aatgacagcg gtagcctgac gttgagtttc ccggatgcga  13020
```

-continued

```
ctgatcgaca gaaagcgctg ctggagagcc tgagcgatat cattctgcat atccgctata  13080
ccattcgttc ttaattaaaa cattgtgata ggcaggctcc tgagggagcc tgtttaagga  13140
gtttttatgc agggttcaac acctttgaaa cttgaaatac cgtcattgcc ctctgggggc  13200
ggatcactaa aaggaatggg agaagcactc aatgccgtcg gagcggaagg ggagcgtcat  13260
tttcactgcc cttgccgatc tctgtccggc gtggtctggt gccggtgcta tcactgaatt  13320
acagcagtac tgctggcaat gggtcattcg ggatggggtg gcaatgtggg gttggtttta  13380
tcagcctgcg taccgccaag ggcgttccgc actatacggg acaagatgag tatctcgggc  13440
cggatgggga agtgttgagt attgtgccgg acagccaagg gcaaccagag caacgcaccg  13500
caacctcact gttggggacg gttctgacac agccgcctac tgttacccgc tatcagtccc  13560
gcgtggcaga aaaaatcgtt cgtttagaac actggcagcc acagcagaga cgtgaggaag  13620
agacgtcttt ttgggtactt tttactgcgg atggtttagt gcacctattc ggtaagcatc  13680
atcatgcacg tattgctgac ccgcaggatg aaaccagaat tgcccgctgg ctgatggagg  13740
aaaccgtcac gcataccggg gaacatattt actatcacta tcgggcagaa gacgatcttg  13800
actgtgatga gcatgaactt gctcagcatt caggtgttac ggcccaccgt tatcctggca  13860
agtccactat ggcaatactc agccggaaac cgctttttttc gcggtaaaat caggtatccc  13920
tgttgataat gactggttgt ttcatctggt atttgattac ggtgagcgct tatcttcgct  13980
gaactccgta cccgaattca atgtgtcaga aaacaatgtg tctgaaaaca atgtgtctga  14040
aaaatggcgt tgtcgtccgg acagtttctc ccgctatgaa tatgggtttg aaattcgaac  14100
ccgtcgcttg tgtcgccaag ttctgatgtt tcatcagctg aaagcgctgg caggggaaaa  14160
ggttgcagaa gaaacaccgg cgctggtttc ccgtcttatt ctggattatg acctgaacaa  14220
caaggtttcc ttgctgcaaa cggcccgcag actggcccat gaaacggacg gtacgccagt  14280
gatgatgtcc ccgctggaaa tggattatca acgtgttaat catggcgtga atctgaactg  14340
gcagtccatg ccgcagttag aaaaaatgaa cacgttgcag ccataccaat tggttgattt  14400
atatggagaa ggaatttccg gcgttacttt atcaggatac tcagaaagcc tggtggtacc  14460
gtgctccggt acgggatatc actgccgaag gaacgaatgc ggttacctat gaggaggcga  14520
aaccactgcc acatattccg gcacaacagg aaagcgcgat gttgttggac atcaatggtg  14580
acgggcgtct ggattgggtg attacggcat cagggttacg ggctaccac accatgtcac  14640
cggaaggtga atggacaccc tttattccat tatccgctgt gccaatggaa tatttccatc  14700
cgcaggcaaa actggctgat attgatgggg ctgggctgcc tgacttagcg cttatcgggc  14760
caaatagtgt acgtgtctgg tcaaataatc cggcaggatg ggatcgcgct caggatgtta  14820
ttcatttgtc aaataagcca ctgccggttc ccggcaaaaa taagcgtcat cttgtcgcat  14880
tcagtgatat gacaggctcc gggcaatcac atctggtgga agttacggca aatagcgtgc  14940
gctactggcc gaacctgggg catggaaaat ttggtgagcc tctgatgata acaggcttcc  15000
aaattacggg gaaacgttta acccccacag actgtatatg gtagacctaa atggctcagg  15060
caccacccga ttttatttat gcccgcaata cttaccttga actctatgcc aatgaaagcg  15120
gcaatcattc tgctgaacct cagcgtattg atctgccgga tggggtacgt tttgatgata  15180
cttgtcggtt acaaatagcg gatacacaag gattagggac tgccagcatt attttgacga  15240
tcccccatat gaaggtgcag cactggcgat tggatatgac catattcaag ccttggctgc  15300
tgaatgccgt caataacaat atgggaacag aaaccacgct gtattatcgc agctctgccc  15360
```

-continued

```
agttctggct ggatgagaaa ttacaggctt ctgaatccgg gatgacggtg gtcagctact  15420
taccgttccc ggtgcatgtg ttgtggcgca cggaagtgct ggatgaaatt tccggtaacc  15480
gattgaccag ccattatcat tactcacatg gtgcctggga tggtctggaa cgggagtttc  15540
gtggttttgg gcgggtgacg caaactgata ttgattcacg ggcgagtgcg acacagggga  15600
cacatgctga accaccggca ccttcgcgca cggttaattg gtacggcact ggcgtacggg  15660
aagtcgatat tcttctgccc acggaatatt ggcagggggga tcaacaggca tttccccatt  15720
ttaccccacg ctttacccgt tatgacgaaa aatccggtgg tgatatgacg gtcacgccga  15780
gcgaacagga agaatactgg ttacatcgag ccttaaaagg acaacgttta cgcagtgagc  15840
tgtatgggga tgatgattct atactggccg gtacgcctta ttcagtggat gaatcccgca  15900
cccaagtacg tttgttaccg gtgatggtat cggacgtgcc tgcggtactg gtttcggtgg  15960
ccgaatcccg ccaataccga tatgaagggg ttgttaccga ttccacagtg cagccaaaag  16020
attgtcctta aatatgatgc gttaggattt ccgcaggaca atcttgagat tgcctattcg  16080
agacgtccac agcctgagtt ctcgccttat ccggataccc tgcccgaaac acttttcacc  16140
agcagtttcg acgaacagca gatgttcctt cgtctgacac gccagcgttt ttcttatcac  16200
catctgaatc atgatgataa tacgtggatc acagggctta tggatacctc acgcagtgac  16260
gcacgtattt atcaagccga taaagtgccg gacggtggat tttcccttga atggttttct  16320
gccacaggtg caggagcatt gttgttgcct gatgccgcag ccgattatct gggacatcag  16380
cgtgtagcat ataccggtcc agaagagcaa cccgctattc ctccgctggt ggcatacatt  16440
gaaaccgcag agtttgatga acgatcgttg gcggcttttg aggaggtgat ggatgagcag  16500
gagctgacaa aacagctgaa tgatgcgggc tggaatacgg caaaagtgcc gttcagtgaa  16560
aagacagatt tccatgtctg ggtgggacaa aaggaattta cagaatatgc cggtgcagac  16620
ggattctatc ggccattggt gcaacgggaa accaagctta caggtcaaac gacagtgacg  16680
tgggatagcc attactgtgt tatcaccgca acagaggatg cggctggcct gcgtatgcaa  16740
gcgcattacg attatcgatt tatggttgcg gataacacca cagatatcaa tgataactat  16800
cacaccgtga cgtttgatgc actggggacg gtaaccagct tccgtttctg ggggactgaa  16860
aacggtgaaa aacaaggata taccccctgcg gaaaatgaaa ctgtcccctt tattgtcccc  16920
acaacggtgg atgatgctct ggcattgaaa cccggcatac ctgttgcagg gctgatggtt  16980
tatgcccctc tgagctggat ggttcaggcc agcttttcta atgatgggga gctttatgga  17040
gagctgaaac cggctgggat catcactgaa gatggttatc tcctgtcgct tgcttttcgc  17100
cgctggcatc aaaataaccc tgccgctgcc atgccaaagc aagtcaattc acagaaccca  17160
ccccatgtac tgagtgtgat caccgaccgc tatgatgccg atccggaaca acaattacgt  17220
caaacgttta cgtttagtga tggttttggg cgaaacctta caaacagccg tacgccatga  17280
aagtggtgaa gcctgggtac ctgatgagta tggagccaat gtggctgaaa atcaaggcgc  17340
ccctgaaacg ggcgattaca aatttcccgt tgggcaattt cccggacgta cagaatatta  17400
acgggaaaag gcaaagcccc tgcgttacgt ttcaaaccgt attcctgaaa taatttgggc  17460
aactatgtca agttgaccaa aaaatgcccg gcaggatatg tatgccgata cccattacta  17520
tgatccgttg gggcgtgaat atcaggttat cacgccaaag gcgggttgcg tcgatcctta  17580
ttcactccct ggtttgtggt gaatgaagtt gaaaatgaca ctcccggtga atgacagcat  17640
aaagctcagt gatgcctgtt cactgaacag acatcactcc atttaggaat gaatcatgaa  17700
gaatttcgtt cacagcaata cgccatccgt caccgtactg gacaaccgtg gtcagacagt  17760
```

-continued

```
acgcgaaata gcctggtatc ggcaccccga tacacctcag gtaaccgatg aacgcatcac  17820
cggttatcaa tatgatgctc aaggatctct gactcagagt attgatccgc gattttatga  17880
acgccagcag acagcgagtg acaagaacgc cattacaccc aatcttattc tcttgtcatc  17940
actcagtaag aaggcattgc gtacgcaaag tgtggatgcc ggaacccgtg tcgccctgca  18000
tgatgttgcc gggcgtcccg ttttagctgt cagcgccaat ggcgttagcc gaacgtttca  18060
gtatgaaagt gataaccttc cgggacgatt gctaacgatt accgagcagg taaaaggaga  18120
gaacgcctgt atcacggagc gattgatttg gtcaggaaat acgccggcag aaaaaggcaa  18180
taatttggcc ggccagtgcg tggtccatta tgatcccacc ggaatgaatc aaaccaacag  18240
catattgtta accagcatac ccttgtccat cacacagcaa ttagtgaaag atgacagcga  18300
agccgattgg cacggtatgg atgaatttgg ctggaaaaac gcgctggcgc cggaaagctt  18360
cacttctgtc agcacaacgg atgctaccgg cacggtatta acgagtacag atgctgccgg  18420
aaacaagcaa cgtatcgcct atgatgtggc cggtctgctt caaggcagtt ggttggcgct  18480
gaaggggaaa caagaacaag ttatcgtgaa atccctgacc tattcggctg ccagccagaa  18540
gctacgggag gaacatggta acgggatagt gactacatat acctatgaac ccgagacgca  18600
acgagttatt ggcataaaaa cagaacgtcc ttccggtcat gccgctgggg agaaaatttt  18660
acaaaacctg cgttatgaat atgatcctgt cggaaatgtg ctgaaatcaa ctaatgatgc  18720
tgaaattacc cgcttttggc gcaaccagaa aattgtaccg gaaaatactt acacctatga  18780
cagcctgtac cagctggttt ccgtcactgg gcgtgaaatg gcgaatattg gccgacaaaa  18840
aaaccagtta cccatccccg ctctgattga taacaatact tatacgaatt actctcgcac  18900
ttacgactat gatcgtgggg gaatctgacc agaatcgcat aattcacgat caccggtaat  18960
aactatacaa cgaacatgac cgtttcagat cacagcaacc gggctgtact ggaagagctg  19020
gcgcaagatc ccactcaggt ggatatgttg ttcacccccg gcgggcatca gacccggctt  19080
gttcccggtc aggatctttt ctggacaccc cgtgacgaat tgcaacaagt gatattggtc  19140
aatagggaaa atacgacgcc tgatcaggaa ttctaccgtt atgatgcaga cagtcagcgt  19200
gtcattaaga ctcatattca gaagacaggt aacagtgagc aaatacagcg aacattatat  19260
ttgccagagc tggaatggcg cacgacatat agcggcaata cattaaaaga gtttttgcag  19320
gtcatcactg tcggtgaagc gggtcaggca caagtgcggg tgctgcattg ggaaacaggc  19380
aaaccggcgg atatcagcaa tgatcagctg cgctacagtt atggcaacct gattggcagt  19440
agcgggctgg aattgggaca gtgacgggca gatcattagt caggaagaat attaccccta  19500
tgggggaacc gccgtgtggg cacccgaaat cagtcagaag ctgattacac aagccggcgt  19560
tattctggca aagagcggga tgcaacaggg ttgtattact acggctatcg ttattatcaa  19620
tcgtggacag ggcgatggtt gagtgtagat cctgccggtg aggccgatgg tctcaatttg  19680
ttccgaatgt gcaggaataa ccccatcgtt ttttctgatt ctgatggtcg tttccccggt  19740
cagggtgtcc ttgcctggat agggaaaaaa gcgtatcgaa aggcagtcaa catcacgaca  19800
gaacacctgc ttgaacaagg cgcttccttt gatacgttct tgaaattaaa ccgaggattg  19860
cgaacgtttg ttttgggtgt gggggtacaa gtctgggggt gaagcggcca cgattgcagg  19920
agcgtcgcct tgggggatcg tcggggctgc cattggtggt tttgtctccg gggcggtgat  19980
ggggtttttc gcgaacaaca tctcagaaaa aattggggaa gttttaagtt atctgacgcg  20040
taaacgttct gctcctgttc aggtaggcgc ttttgttgtc acatcgcttg tgacgtctgc  20100
```

-continued

```
actatttaac agctcttcga caggtaccgc catttccgca gcaacagcgg tcaccgttgg  20160
aggattaatg gctttagccg gagaacataa cacgggcatg gctatcagta ttgccacacc  20220
cgccggacaa agtacgctgg atacgctcag gcccggtaat gtcagcgcgc cagagcggtt  20280
agggcactat caggcgcaat tattggcggc atattacttg gccgccatca gggaagttct  20340
gagctgggtg aacgggcagc gattggtgct atgtatggtg ctcgatgggg aaggatcatt  20400
ggtaatctat gggatggccc ttatcggttt atcggcaggt tactgctcag aagaggcatt  20460
agctctgcca tttcccacgc tgtcagttcc aggagctggt ttggccgaat gataggagaa  20520
agtgtcggga gaaatatttc tgaagtatta ttaccttata gccgtacacc cggtgaatgg  20580
gttggtgcag ccattggcgg gacagccgcg gccgctcatc atgccgttgg aggggaagtt  20640
gccaatgccg ctagccgggt tacctggagc ggctttaagc gggcttttaa taacttcttc  20700
tttaacgcct ctgcacgtca taatgaatcc gaagcataac aatcatgttc attcccactt  20760
tgtcatggat gacaaggtgg gtttttcgga tgtgtggaca gagacccgta cagggtctct  20820
gtccagttaa tttttggatc aagaacgaat ggtgtaacgg atatgcaaaa tgatatcgct  20880
caggctgagc aataagcttt tctgtttacc actgataccg ggaaaactga gggttaatgt  20940
gcctgtatcg gccacaggaa gcccttcaaa tggcaggtac ttagcatcat tgaaatccat  21000
ctggaattga ccactgtcat tcatgccatg tgagatcaca atcgctttgc agccacgtgg  21060
catcattgta ctgccgccat aactcagtat tgcccggaca tcctgataag gccctaaaag  21120
ggcaggtaac gtcacactga tttgtttgat acggcgtgta ttacctaaac cgtcaggata  21180
atcggtagca atattcagat ccgataattt gaggctggct tgcagttgtg tcccttcgac  21240
gttcaaaccg ttaagcgttg tgcctgcact gccttcacct gcattgacta actcagtcac  21300
tttatctttt aaaatgaaac tattttctgt cagaccagca tacacttcag ccagagaaac  21360
ggttctggtg acctccagtg cccgttcatc tttttccaaa tagctttttt ccatctgtgc  21420
taaattcagc atcagggttt cacccgctaa taaacccgca taagtcccat gccaagcacc  21480
tggtttaata aagtgtgctg ccgcattatt caattcatac tgataagttt gctctgccat  21540
taaacagagt gagaccgcca aatcataaaa ctgataataa atagcggaca acgttccacg  21600
gagccagttg tatagcgctg cattactgaa tttactttgc agaaaggcta actgcgcctg  21660
agtttgtgcc tgctgagttt ccagatagtt tttttgtaat actgccgctt cacgacgtac  21720
agccagcgtc gctaattgag catcaatttg ttttatctca gcttccgcat tattgcgctg  21780
aatttcccac tcttgccgac ggcgacggta tatttctgat tggctgattt tgtctgcggc  21840
aatacgtgtt gctgacgcag aaatttcgat accaatcgca ctggcattga aaagcgcccc  21900
aaaacgggaa cctcccacag caaaaccgta aatattgggg acgagatctg ccgcggcggc  21960
ggccatatgc agggctgtgc cgctggtgct caagaccgat gaagagaggt aaagatccat  22020
cgcttgtttt tcaccagcgt taacatcttc gtcgtacagc gtattgaaac tgtcaaaacg  22080
agactgtgca ccatgacggc tttcttgaag cgccaattta tcagcatcaa tttcagccat  22140
gaccttatcc tgcattttaa tactttgcag ggctaactca ctgccttgag tttgcagtat  22200
ttcagccaag gcttctgcat cctgccgttc agtaatgctg agcagggtat tgccaaattg  22260
tatcaactgg cttacccccc acttggcatt ttccagaatc accggaaaac ggtacatcgg  22320
catcactgca tgaggtaaat cgccgccgcc ttgtgaagca gtgatggcag cactgagtaa  22380
catggacgga tctgcgggcg tggcatagag agataatgac agtggctgac cgtcgattgt  22440
caggttatgg cgtaagttat agaggcgttg cgtcaatgtc tgccagtaac cttgcagttt  22500
```

-continued

```
tttattaatt tgagggagga acaatgcggt taacgaaatt tgccgtacgt ttcgtgggta  22560
atgcagcgcg ctgacgcagt tgcagcattt tatgttgata atgatgccgc attgtttggc  22620
tggcagcttc ttccagccgt ggctctgacc aatcgttatc caatgaaaaa taaggctcat  22680
cacccaataa agtgagcgcc tgtacatacc acattttagc ttcgtttaag gtatcacgtt  22740
caagctggcg ataggcgcta tctccgcggg taatcaacaa atccagcatt ttcataaagg  22800
tagccacttt atagtgcatc ggatcatgct gggcaacggc gtccggatcg accgaatcca  22860
gcggattggc attccaggac gtatcttcct ccaatgggcg gacgttccag taataatcct  22920
gcatttcacc ctgaaccgaa tatccggtcg ggttcagata tagcgcagcc agcgtgtcga  22980
tccggtaaaa tctgctcttg caataagcgc tggaatacca tcatgggcgt tgtaatagaa  23040
caatcccaag aaatagattg cattggcgcc gtttgaaatc catgggttca gtgttatttt  23100
tcatgacacg acttgaatac cccttttata ttttttgata tttttttacta tcccctgttg  23160
tgtcattccc gaatcatgat cggcatcatt agtgaatata aattgatttt tcgtctcatc  23220
aaaataaaag aaagcagatt cccaggattt gtcatagata atttttttgt acccaacccc  23280
taatctgaca ccttcacgta tgtaatatcc tttagcatag ggaacaaaga gcgttactgt  23340
ggtttcaata tcagataaca ttccttcgta ataaggttgt ctggcagaat tgccatcaat  23400
attcccaata tggatcttaa accaacgttc atcaccatgc tcctctttat tgtagggggg  23460
caacttaaat gtcgcataaa acccttcacc taattgcggc tctggtaaat tttgcgtttc  23520
catacttaaa acattatcaa taccaatatt ggctctttca gctaattttc tggaaaataa  23580
agtatttaac cgggttctgt aagggccaat ctgcatatat tgtgtgcctg atggcatttt  23640
atgcagtgat ataacgttac ttgtatcttt ggattttagt tttatatgaa ttggcgattc  23700
aataacaata tcgttataac cgccgtcggg ttgcttaata ataaactcgc tcaccagagg  23760
aatatcatag ccttcaatat caacttttac ttgattaaaa tcatatacca tagggtcaga  23820
ttcgtgtgaa ggtttagatg ccacatggtc ttcagcattt aactccacta gaatatcaga  23880
gccatttttt aataaaaaac taatgttttt atcttggatc tgttcgatca tagatgaagc  23940
aagttttatt atctgtggct ggttgaacat aaatacaccc atggatcctc gcgaaggaac  24000
agtgccgcaa tatttcccat gttattaatg attgaaacat cattagtaaa tgattcacat  24060
atagtatgcc atactcctgt gttatctttc caatctaata ctatgttagt atcaagtttg  24120
aattcagcat catctgattc ataatcataa tttataccaa ctccaatttc tgattttcta  24180
ggaatttttt ccttggttct tagatgcatt aacactctaa aatattcggc atttttaaga  24240
tcgatggaaa taataaaatc caaagttcca taatgaaaaa cttcttcttc ttttccaagc  24300
atttcatcat gtctatcata atcaaataaa ataaccgttt catcttctac catcgataac  24360
aggtatttaa cctcatcatt atatatattg ccttttgaaa aattaatttc cattgaagga  24420
ttgaacgtta aattaatatg accatttcct ggtgatatat acgagagatc aaaaatattt  24480
ccggtaaaac tggctaattt attttttgtg gttatagatt ccttatattc ggccaaataa  24540
tctgtagcaa attgattgtt gactttgtat tctgtcctgg tatcaagttc tgataatgtg  24600
ctcttaacaa tggcgtctaa atcattttct gtgagaatgg ataatgtcat atcagggtta  24660
atggtcatcc cttctcttgc aggaagacta ttaaaagaat aattgtcttt tttctcatgg  24720
aaataaacaa taatgacgtc tttttcataa tcagaagaac aatacatacc aatgctggct  24780
tttttattga tcaggttttc tattttatca gtcacattaa aattaaacgg tgagctccag  24840
```

-continued

```
ctgccatcat aacgaatatg tgacagtttt aatatataat cagtgatatc tatcttgcca  24900
tcttcacttt catttttcag ctctttttgt tccagccaca gtaaatacaa acgagacttg  24960
taaataacag gtctgatatt ttcctgccat acattgatgg gtatttcaat ttttttccat  25020
tctccccagg cattggcagc aaattgaccg tgctggcact tttggtgatc gacattgcgc  25080
caataaatata ttctgggttc tgtctggcta taaccaatta aataagtgag cccctcattg  25140
acattaatac tgtcatgata tccgctaatc acctgcaagt tagcgacatc ttcaaatgcg  25200
gtcagataat ttttaaagct atcttcaacg gtatcgatat ttaactgact ttgggaaagt  25260
tgctgtaaca ggttgttcat catacctgtc tgaccaatac gaatcgtggg gtcgatatag  25320
ttttccggat aataggccag ttcagatacg ccggcccagg tgctataccg tcgattgtag  25380
gtttcccagt cgcagaagaa ctgacgggtt ttcactggct ttgatacttt tccttcaaca  25440
ttattcaacg cccggttgac atataactga atgctggcaa tggcttctgc cacacgggtg  25500
gttttcactt gggcagaaac ttggttatca atcagcagat agctgtacaa ctcatcccgg  25560
ctcttaatct gttgaggtgc accatttttg atgtagtaag cactggccgc tgtcgtcgtg  25620
gcttcatcca gccatgcctg aagctggtcg gattgttgac tgttcagtcc cgcctgcaac  25680
aaagtactgg cggcttgcca atcatcaaat gttggcatcg gggtttccgg ttcaccgaca  25740
tattttaatt ttatgagtgc agcaacacca tccggggtaa tacccaatgt agcagcgaca  25800
tccagccatt gcagagtgac atctataagt tctccagttg gtaaaggtat tcactcccaa  25860
accggtctgt tgcaatgctt gtgtcacaac ctgagcatca aaattttaac gccaccgcca  25920
aattgttcgg cagtcaacgc tcctaagttc caaatgctgt taagattctg tcgcgtagct  25980
tcacaacgca tgatcacagc atggaagcgg gtcagcgctt gcaaagtggg gagatcatgt  26040
tgcagtgctg tggtttctga ttggaatttc tccggttttg tcaccaacag ggtcagttcg  26100
ttttcgctga gtccaatatt gcgcacaatc agagaaagtt gccccagtac ctgacaaaaa  26160
gccaccatgt tgctggtttc attctctgag cgatcacggt tagccgcaat aatcatgaaa  26220
tcatcgaatg tcagtccttg tggtttttatc tgattaatcc acagcaaaat agtttctgct  26280
gttttggctg aatccatttg aatgctggca gcaatcagcg gggcagctgc acggatcagt  26340
tcgtcatcac cgagtgaaag tgttgataat ccattactta gtgtcgtgat aaggttttca  26400
atatccggcg taaggacagt gctgtaatta tccgtggtca tcagaaacac atcactgaca  26460
gaccatttct gtgttgtcag ccactgggtg cattggaaca gaaagctgat taattgcgtt  26520
aatgctgtat cagaaaaaag ggcaattttc gtgttcacat agggagaaac cgacaacaac  26580
atggataatt cattcactgt cagatgatga atgtctgcca gcagacgaac gcgataaagc  26640
agagacaggt tctcgatgga acacataaat tctggatttg ttccgccatt agccagtttc  26700
cataatgtat acagttcagt atcattcact ctgaaagcac gtttcattat tcccaaataa  26760
aaatggtttt ttgattcacc gggggttaaa tccagtttgg tattatcagc agaaaactct  26820
tggccattta atagcggtgt attgaacagc attgtaaaat gactgggttg ttgtttagtg  26880
gaatattggc tgatatctga atgacacaat accagcgcat cgctgacgct aatattatag  26940
tgctgcatat aatattgaac ataaaacagc ttacccaaca cattgctgtc aatggttaag  27000
tcatcataaa tactttctat tacttgccag atatcttctg gagatatgcc tgtggcttta  27060
tacaaacgaa tcgctttatt cagctttaac aggaatatat caccgggaac tccatcattt  27120
taaagtgtgc attggcattg atagcatccg acggatttgg ttaactcgcc ataagcggag  27180
tgttataccg ttggtgattt gctctgtcgt caatttaatg ggaatactgt aatgggtatt  27240
```

-continued

```
agcaatgggg acgaaatttt tatcttggta tatatattct ttatctccat tctggagacg  27300
aaaatccaag tggtcaggtt ctgttttttt tacactgaaa ttatatttgt attcattttc  27360
tttgattgga attagctctg catagtttaa atgtgaatcg tagaaatctt tgcgggttcg  27420
cttaatcaat cttgccgttg ccgtatcatt cccgtcattg accaatgtta tcagttgctc  27480
attcttatac tgttgatttg tatttttctt accgaaggag agattgacaa ataaactgag  27540
ttcatcataa gacaaatcgt agtagcgagc caaagaagca taactcttaa aaatcagtac  27600
atcatctgta ccgaaatttt tcttcatcag ttctgttgaa ttttccggtg taatttcttc  27660
tacaaggatt tgatacaatt caggcgatat atcagtctta atagccagta gcgatgttgg  27720
gtccattaat tccgctacgt ctgtattacg gctaaatgcg gtgaggtttt tatcttgcaa  27780
taaaattgcc tgacgggctg actcatacgg cagatgatag ggtgtcatgc cggtttgccg  27840
gtaagtggac aacattttca ttacaccgtt atagtcagtt ttctctaacg tctgaatatt  27900
atgcagcagt aattcattag ataaggataa tgtggaaatt tcttcatcca tattattctg  27960
tgtcagtgcc agtgaagcaa tgtcggggcg tcgtttattc aggtgatatt gagaattgtc  28020
aggatgaaaa tctttcgctt cccgatataa ttctgttaaa taagccgctg gtgaaaatat  28080
ggaagcaatt gatcccggtt ttacaaaacg gtgggcgcgg ccataaaacc aactgttgta  28140
actattgttt agggttgacg gtgtaatatt aaggttagtg atattagcca gttgtggatt  28200
agcacgggac aaaatgcgca gttcttcaag tttattctgt tttgattcct gatgagcctg  28260
ttgatataaa aagtctgttt ctcgccacgt cagagttcca cttgtcctat gacgaaattc  28320
gctgaaagac ataaacgaaa tgtttgtcaa taataaagta tcaccagcct tttctatttt  28380
atcttatcta acagttcatt aacttttatc atataaatcc ttaagttatt gtcaatttaa  28440
tgattaatgg tttttaggtg gagattatta taatctgata ggaatattat ggttaattaa  28500
attgatactg atttatcgct ctattctttc aataaaaaat aaagaacttc cctataatac  28560
atggatttaa ataatgaata ccgtatgtta aaaattaaat tttaacaaac tttcatgaaa  28620
aaattcaact caacaattgt ttaaatattt ttaattgtgt ttgtgctgtt tgaaaaatga  28680
atgactaata tttatctatg aaagattatt tattgaggat gtcttgcttg gtttcagggg  28740
gctacgttgg agtcagataa atgtgtgcaa aaagaaatcc ttaataaagt tgcgtaatta  28800
caaaagttgg tatatcgtga caagagtgat agtaatgtca cataatttat tgaatacccg  28860
aacctcgcaa atgcggggtt tttcttcgca taatcaaaga gaaagctatg aaaaaaacac  28920
tgattactct tattctcagt accctttctt ttggtgcttt ggcacagcag ggtggcttcg  28980
tttccccgga cagcacagac tatactcagg gtggatttaa aggtccaact cccaacctga  29040
ccagcgttgc tcaagcaaaa tcttttcgtg atgatgcgtg ggttgttctg gaaggaaaca  29100
ttgttaaaca ggttggtcac gaactctatg aattcgcggc cgcataatac gactcactat  29160
agggatcgct tattacggac ttatccggaa agctatctgg aacccctgtt acgcctgaat  29220
aaaacagaat tcagggataa cagtggttct gtttatgttg acattgatga taagcgctgg  29280
atgggtctga cggccactcc aactgacaaa gttcgtatcg aaggtgaagt ggacaaagac  29340
tggaacagtg ttgaaattga tgtcaaaact atccgcatag tgaaataact caagcacttt  29400
gaatatagcc ccgcactcgc ggggtttttt gctttctggg agtcggaagt ttaaccgtag  29460
tgacgaggat caaaactaag ttaacggcag tggtcactga tttggtgcat aagttatcaa  29520
aagttaaaaa tcaaaactta ttttttattt aatagaggaa tgtcaccctg taggtgaata  29580
```

-continued

```
acgttgacgg atgtaaatat acagtattat agtcctttga tatgttatta aattgaaaaa  29640
cctttaaact atattcgggg gaaattatta tgtcagatgt tcgtaatatt attaatgttg  29700
ataacaattt tggttgtgaa tataaagcgg atttatttaa ataagttttc ataattgtga  29760
tacacccatt tttctcatcc ccggtttttg ctgttgtaag gaagcggttt ccatgaagat  29820
tttgacatgg ttaagcaact gccacataaa ttggcagcag tggtttcgtg tcacggtttc  29880
atgcaaggat tgccatagac gttcaatttt attcaaccac gggcaatagg tcggtaaaaa  29940
gagaagatta aatttgggat tctttgccag ccaaaccctg accttccggc tcttatgaat  30000
gcaatagtta tctaaaatta acgtgatggt tttggcatta acatattgat tgttaatttc  30060
atctaacaat ttgataaata aatctgagtt ctttctcaag ctaccgacat aagtgatttc  30120
tttcgttttc gcgttgaggc aattggcaag gtagtgtttt tggttctttc cgggggtaac  30180
aacacgcttt tgttgccctt tgaagcacca gtctgcaccg attttcgggt tcaggttgat  30240
gtccacctca tcctcataga agaccgggtg tttctcttga ggcattggat aacgtctcgc  30300
tgatttttgc catttttca tcatactcag ggtcaggcaa ttttacggtt ggtgccgccc  30360
ttcgccaaac gatgcccgtc cggcaaaagt agcgatagag ggtactttga gagagcgatg  30420
tattcagtag ctcattgatt ttaagtgtaa taagctcaag gctccatcgt gaacggagat  30480
agccaaaatg ttgtggcgag tgctgtaata agaaagaaat gactgtgaag agcggagcta  30540
agttccagat ggcaggcctt cccgccggga ggcttttaag tccttccaac ccgtataatg  30600
ttaaccaatt tacccaacga tgaacggaag aacgtgaaca gtgaagcgtt ctggaaacgt  30660
gagaaaccgt actcccttca tgtaacatca agagcgcggt gaagcgacgt gcatagtcct  30720
tatcccgggt tttctggata gctttttca tcggacgtcg ttcatttcgg ggtattgatg  30780
ttatgattgg catgactcag tccattttgg gatttgtttt gatttggcga ttaatcagat  30840
cgcgaaaatc ggactgagtt cccttcaagt gatctactat tttgaaatct tatttaatca  30900
ggagtcagca aatgagttat tccccataat acctgaccat gtggttgttt atccgggaaa  30960
tgattcatct accggtggta tgtggattcc ttggtgcgat agtcagaaag atattgactc  31020
tggccattat atcaaagtta ctttcagtaa aaaggacgct gctgatattg tgaactacat  31080
gtttcaacat ggcagttatg tttattttac agacagtagt aaacaattta gcaataagca  31140
aattatgtct ggtgattcag ctaaaggcaa aggggattat aagcttgaaa ttaaaacaaa  31200
cgggaacctt ccactgatgg tattgaataa atattgattc attattattt atggataaga  31260
aattaagttt atatttcatc tggtttctgc aattaagttt taaaaattaa ttctactttt  31320
tttatggttt tatatttaat gccaatcata ttatttttct tataataatt gatagtttat  31380
ttatatagta aataaattct gttggatgtg attattattg tgagacggta ataattaaca  31440
taacagaaaa ttcatggtta ggaaattcaa tcaacttttg tccggtttcc tgaccatgaa  31500
gagctgtatt tactgtagaa ctcgcattga tactggattg attagccgga cgagtgttgg  31560
gtcagcagat aatatgttgt atattggctg tggatttttc agcgagatga tagctttggc  31620
agtaaaggcg attaataacc gataaaacag agagacggat tgtggccagg aaagcaaaaa  31680
agcctcacca tgacgcgtta ttcaaacatt ttttaaccca accagaaacc gcccgggaat  31740
ttttatccct ttatctgccg gaagcgatcc ggtcagtgtg tgatttacca cactaaaact  31800
ggaaccggca gctttgtgga caggcaatta cgtcagttgc acagtgatgt gctgtattct  31860
gtcgagacaa cccacgggga cggttacatt tattgcctga ttgaacacca gtccacgcct  31920
gatccgttaa tggcctggcg gctgatgtat tattcgctgt cagccatggc tgcgcatctg  31980
```

-continued

```
aaaaaaggac atactgaact ccctttggtc gtccccctgc tgttttatca tggtgaggtg  32040
aggccttacc cttactcaaa tcgatggctg gattgtttta cactctctga acacgcggct  32100
cacctgtata atcagcccct gccgttggtg gatatcagtg cgctcagtga tgaagagatc  32160
ctgacacata aaagcattgc cttgatggag ctggtacaaa aacatatccg ttgccgggat  32220
atgctggagt gggttcccca attggtggcg ttgttgaatg ccggttataa tagcgccgaa  32280
cagcgccatg ttgtgttaag ctatatttta ctgaatggac atacgctgga tctcgcccag  32340
tttgtccatc aactgactga acaatctccg gagcatgaaa ccatgttgat gactattgca  32400
gaacagcttg aacaaaaagg gcgtgagcaa ggccggacag aaggcagaac agaaggcaga  32460
gctgaaggac gggaagaagg caagctggaa acggcgcgcg cattattacg gcatggtgtc  32520
agtctggaca tcattgtcac cagtaccggc ctgagccggg agaaaattga agcgttaaag  32580
cattaaatgg atacgctttt tcacagcagg atatggtgac ccctgtgagg ccaccggaaa  32640
attttattta ctacgattta cgacgggtta ctttaggaag ctgaatgaga cgtcctttgt  32700
tatataacgg tcccatatca atcttctctt ttccgcgtac aggtaagtaa cccaaacctt  32760
cgtgagcagc atttgccaac aggccatcat cctgatcgcc tgaccaagag aagatcccgc  32820
ccaatttcat tttggttgca taaattccct tatgcagcac agtgcggggc gtatccagtg  32880
aaatccagtg accaccgtca gcattaaaga gtgcgtcagc gtcggtttcc gtgtctgtca  32940
ccagttcaaa ctgatttttc ccgcgtgcaa tttcatattc cgcatcgtat tggttattca  33000
gcagacagaa gaattccgga gcaccttttt ccatcgtgcc cagtggctct cctgttctgt  33060
tatagcggcg cgttgtcaga tcagcaccca gacatgaacg tccatagtta gcaaatccga  33120
ggtgaatttt ctccggttgt acaccttgtg acagtaaaaa gcggatcgcc tcatctgccg  33180
agtaatccat gtcccgatca ggattgggcg gaggagggtt atcgccgtca tattcatatc  33240
tgggggggata caggttagta tggtgaccga tgtattctgc ccaaccggta ccaaagaagt  33300
cgtaggtcat cacaaagata ttgtctaaat aaggtgcgat ttctttgaag ctggacttct  33360
ccattttggc aacgacggcg ctacaggcta tcgtgatttc tttacgggcc cgggttccaa  33420
aggcgatgtt cagtgcttca cgcagctctt tcactaacaa aacatagttt gggccatcat  33480
gttccgggtc gaattcatta ccttcttcac ctgtggcgcc ggggtattcc cagtcgatat  33540
ccaccgcagt aaacatggga aaacgccggg aagaagtcga cgatgctact cacaaatgta  33600
gcacgttgct caggatcttt ggccatcaca gagaaatacc ctgacatact ccagccgccg  33660
atactgaatg cgagttccag cttatgccct gcctgttttg ctcgcgcttt cagattacgc  33720
aatcccccca gtaaaccgga ggctgcatcc tgattgtaat attgcaagaa attcttcggg  33780
ctggcatcac ggcgctgatc cgcgtccaga ccgacattgc gtgtggtgcc taaatcacca  33840
taaggatcaa cgggtacaat atggcctaat gtaatagggg caatctggcc actgctggct  33900
tctgcttgcc ggttccaccc gtcaacaacc tcattaatcc gttcggataa cttgcctttg  33960
tcaccgttga cggccataaa actgaaaatc aggcggtcgt aggcggtagg cgggattttt  34020
tccagatcaa aaccacggcc gggggcatcg tcgctggtca gcgcagtgtt atcctgggtt  34080
tctggcgaca aacgcgcatc atactggcac cagtcagtaa tataggcaga gactttaggc  34140
agcggttctg tattttccgg atcaacttca tattcgttgt acagggactt ggcaacacgt  34200
gctgaagaat aactcaaagg agttccgctg ccgtcaggtt tatatcccac cttctgatag  34260
gtttcttctg tgagtgcatc atattgcaat acctcggttt tttctcccgg cggtacatca  34320
```

-continued

```
ggcgtattgg ggttaccgtg atcggcaatt tcttccggtg tcgcctcacg gacatattgc  34380
caggcattct cataaaccgg taaatcaggt gaaatattgc ggtcgggaat atgccagcgt  34440
tcaacccagc cgatgttttt aaaaaccgcg ctatcataaa tgacatacca ggtttgacca  34500
ccagattgat tctgccaggc aaccagagat gcgcctactt cgctgctggc gtcagacatc  34560
gctttaattg aagggtatcg ataaacattt tgagacataa tttcacttcc ggccccgtta  34620
tattccgggg ccggctcctg atatcagtta gaattgtctt gttttaattg atgtttattc  34680
agacggctac gaacctgctg gctgaactca ttacttccgc cactcacatc acgcgcggta  34740
taacgcagat ggaggataat atcgctcagc gactccagca gctgatcctg atcggaaccg  34800
aattccaact tccactgtga aatggcgcct gtcccttcaa aaggcaggaa aagttcatca  34860
tcaaaattga gcctgaacat gccgctgtct tccatggccg ttgaaatcac cacaccttga  34920
ttagcctgta cgttcagcaa aacgttttcg ggtttggtgt attccaaggg gttaagcaaa  34980
taatcgatag tttttaagtc agcagtactg taaagcgtat tgctgagttg taccagtgaa  35040
gcccgtacat cttcataagg ccccagcaat gcgggcaatg acagcgctac ggtttttata  35100
cgccgatcag cgtgggtcgg ataatcgcgc aagaacattt cggcgctcag taagaaagtg  35160
aatgaacccg tactcttgcc aatttcccac tgtgatgatg tcagtaatga ttttaccgat  35220
atggttttta tgatctccag acgtctggtg ttatgttgca aatacgcctg atccatccgt  35280
tgtaaggcta atttcagatg ttctccgacc agcagcccct gataaagatc attccagaga  35340
ccactttgga cgaaattcat atcatactga cctgtttcgt actgccagga ggcttcggcc  35400
agtaaacaga gggaattaac cgcatcatag gcttgcaggt aaagccggag atttggctga  35460
tcatccacat gtataacgca tcattggtan anttgttcnn nnnnnnnnnn nnnnnnnnnc  35520
ccgaagcata ccgccaagac catccccccg acggccagac cgaaaatatt gggaaccata  35580
tccgccacag cggccgcagt ggcggctgac tgggcagcga tcacaccttc agccgctctt  35640
gattgtaatg cgataacttc ctgctcggtg atggagatgt tttcatcata gagcgattta  35700
tagtgttgct ggcgctcctg agcggcccgt cggctgatgg tcagtgcatc caatgaagcc  35760
tgttgcatgt caatcgcttg ctgttgcaga ttgcgggtaa agctgtacag ccccagttgc  35820
tgctgcatac ggaagtgttc aaaatcggta ttgtcttttt tctccagcaa actcagtaac  35880
gtgctgccgt actgaatcag cgtttctgcg gcctcttttg cccggctcat gatcggggtg  35940
aaacgataat tcgggattgc ccggcgtttc atgcccgcca tacgattagc cacaacacgc  36000
tggtaacgct gcctgagcag atcttgcggg ctgatgggtt catcgtataa tccggccgga  36060
aactctttac catccaaggt caggttatga cgtaagttat atagacgctg atccaacatt  36120
tgccacagtt tgagatattc cgtatcaaca ggtttgacaa ataaatcaga cggtgcggca  36180
gagacggatg tatcatatgt cacaggcaga agtggcacgt tgctgacagt aagcattaac  36240
tcctgtgccc gtgcttcact gttttcatac agagccacat cttgcagcgt acggggttgc  36300
cagtttgccg cgagcagaat atcagggctg gtacccagta acatattgac ggagtcatag  36360
atctgcttgg cgacagtacg tgcactggat gtcagcttac ggtattccat gtctccctga  36420
tctaacagat tcttgacata gaaacggaat attgctttcc ggtagtgaat gggttcactg  36480
gctgcaatgg catccggatc ggttggttca attaacatcc ggtacacggt gggtggagga  36540
tcaataattg gccgtgaatt ccagtaacgc ggtttacctt ggttgctggc ctgaacaagt  36600
tcatcttcca gcggattaaa aatatagtgc agccattcgg tggcctcttt taatcgttgt  36660
tctatattca gtcgccacgc gaccagaaat ggcatatgga aaaacagttc ccagaaatag  36720
```

-continued

```
atcccatttg cgccatttaa atcaatcggc gtagggaatg aaccgggtat aggctgttcg  36780
gtaataagct gtgtattcca gctcagtacc tgcgggatac cctgactggc aatggcgatc  36840
agttttttg caaacagtgt attaaggcga atgttttgtg gcgcgttatc agtttcatct  36900
gcggggaagg aaaggaattg cacctgatcc tgttcattga gtttaatcag ttcgcgaata  36960
tgcataccga ttctgaactc ttgagtacag ctggcacttt cattgccaac accacctttg  37020
ggcttaaaga gaagttcggc tttcagggtg attcgattat ccgaccccag cttgattgat  37080
ggataggtta aatcaagaac tttttcgctc agtaccagtg gttgttcatc caagacagta  37140
ttatcgtgca tcagccggaa agaaccgttg taatattgat gatcttctat cgcaccaaac  37200
ttaaagtcag attgagcgac aatctccagt gtgtcatcag tgccatgaac aaaattgaca  37260
atcagtttga tactgtcttt gccgaaatca gggttcattc cggtttggat tctccggcaa  37320
taggaaagcg ttcttcccgg gttgccggat agagcaccat agtacggtaa tcgataggat  37380
tgccttaagg catccttgtg ttcacgtgag taataccaga ccaggttgcc gacatatttt  37440
ccttttcgtc catcagcata ttggtcatcc ggcaaatcag taatttctac cagcagtgta  37500
tcgcagacat aaccgaaggc ttcgtcataa tcataatcct tacctttctt atctgtcccc  37560
tgaagacgga caaacggaac cagagccaga aacgggttat gcgggtcttg ctgtatatcc  37620
atcacagcaa ccatctgggc catccggtat tgcagatgtc ttcgcgcaga atggtgggtg  37680
tactccagct gccatcatat ttggcataag cgattttgat ccggtcagga acggtgtggg  37740
aggaacccaa tcacccgcac taggctcaac gttttggtta tgcagtgata acgcagttgt  37800
atctttagtt tcagactgtt cttcaacttc cgtccaggca atatacaggc gattattcag  37860
gaaaatgggg cgtatcaaat tggggtctac gctgcccaat ggcaggtcaa taggtttcca  37920
ctcgctccag gcattgggag ataacgcatc ggtatcagga tggcgtatcg aaagattcag  37980
tgaacgccag taatattggt atggctgtgt acgggtacgt ccgacaaaga agaacttatc  38040
gcgtttgatg ttaacaccat cttcataacc tgcgataact ttcaggttac tgacatcttc  38100
aaaattattc agataaccga gcaccgcttg ttgtacagaa tcttcggtaa tttttccctg  38160
attaagggca ctttccagtt ggaagaagaa ttctgtttta ttcaggcgta acaggggttc  38220
cagatagctt tccggataag tccgtaataa gcgatccc                          38258
```